(12) United States Patent
Sasaki et al.

(10) Patent No.: US 7,745,988 B2
(45) Date of Patent: Jun. 29, 2010

(54) 3, 6-DIPHENYLCARBAZOLE COMPOUND AND ORGANIC ELECTROLUMINESCENT DEVICE

(75) Inventors: Masaomi Sasaki, Susono (JP); Masafumi Torii, Yokohama (JP); Toshiya Sagisaka, Yokohama (JP); Takashi Okada, Yokohama (JP); Shinichi Kawamura, Kawasaki (JP); Chihaya Adachi, Chitose (JP); Yuuichiroh Kawamura, Chitose (JP); Kenji Muneuchi, Yonezawa (JP)

(73) Assignee: Ricoh Company, Limited, Tokyo (JP)

( * ) Notice: Subject to any disclaimer, the term of this patent is extended or adjusted under 35 U.S.C. 154(b) by 284 days.

(21) Appl. No.: 10/933,230

(22) Filed: Sep. 3, 2004

(65) Prior Publication Data

US 2005/0084711 A1  Apr. 21, 2005

(30) Foreign Application Priority Data

| Sep. 5, 2003 | (JP) | ............................. 2003-314495 |
| Oct. 31, 2003 | (JP) | ............................. 2003-373735 |
| Oct. 31, 2003 | (JP) | ............................. 2003-373745 |
| Aug. 25, 2004 | (JP) | ............................. 2004-245423 |
| Aug. 25, 2004 | (JP) | ............................. 2004-245438 |

(51) Int. Cl.
*C09K 11/06* (2006.01)
*H01L 51/54* (2006.01)
*H05B 33/14* (2006.01)
*C07D 209/82* (2006.01)

(52) U.S. Cl. ................. 313/504; 257/40; 257/E51.047; 313/506; 428/690; 428/917; 548/440

(58) Field of Classification Search ....................... None
See application file for complete search history.

(56) References Cited

U.S. PATENT DOCUMENTS

| 5,382,477 | A | 1/1995 | Saito et al. | |
| 5,981,124 | A | 11/1999 | Shimada et al. | |
| 6,103,435 | A | 8/2000 | Shimada et al. | |
| 6,184,362 | B1 | 2/2001 | Shimada et al. | |
| 6,271,356 | B1 | 8/2001 | Shimada et al. | |
| 6,562,982 | B1 * | 5/2003 | Hu et al. ..................... | 548/440 |
| 6,670,054 | B1 * | 12/2003 | Hu et al. ..................... | 428/690 |
| 2002/0045061 | A1 * | 4/2002 | Hosokawa .................. | 428/690 |
| 2005/0127823 | A1 * | 6/2005 | Iwakuma et al. ............ | 313/504 |
| 2005/0158578 | A1 * | 7/2005 | Iwakuma et al. ............ | 428/690 |

FOREIGN PATENT DOCUMENTS

| JP | 08088083 | * | 4/1996 |
| JP | 9-310066 | | 12/1997 |
| JP | 2000286056 A | * | 10/2000 |
| JP | WO01/072927 | | 10/2001 |
| WO | WO 2003/080761 | * | 10/2003 |

OTHER PUBLICATIONS

Machine assisted translation of JP 2000-286056.*
Machine Assisted Translation of JP 2000-286056, (2000).*

* cited by examiner

*Primary Examiner*—D. Lawrence Tarazano
*Assistant Examiner*—Brett A Crouse
(74) *Attorney, Agent, or Firm*—Oblon, Spivak, McClelland, Maier & Neustadt, L.L.P.

(57) ABSTRACT

A 3,6-diphenylcarbazole compound, which has a specific formula and realizes an organic electroluminescent device having high durability and high luminous efficiency. An electroluminescent device which includes an anode; a cathode which faces the anode; and at least one layer including a luminescent layer, optionally a hole transporting layer and an electron transporting layer, which is located between the anode and the cathode, wherein the at least one layer includes the 3,6-diphenylcarbazole compound.

10 Claims, 32 Drawing Sheets

ITO/TPD/CBZ1+Ir(ppy)$_3$/BCP/Alq$_3$/MgAg/Ag
(110/50/20 [6wt%]/10/30/100/10 (nm))

ITO/TPD/CBZ1+Ir(ppy)$_3$/BCP/Alq$_3$/MgAg/Ag
(110/50/20 [6wt%]/10/30/100/10 (nm))

ITO/TPD/CBZ1+Ir(ppy)$_3$/BCP/Alq$_3$/MgAg/Ag
(110/50/20 [6wt%]/10/30/100/10 (nm))

ITO/TPD/CBZ2+Ir(ppy)$_3$/BCP/Alq$_3$/MgAg/Ag
(110/50/20 [6wt%]/10/30/100/10 (nm))

ITO/TPD/CBZ2+Ir(ppy)$_3$/BCP/Alq$_3$/MgAg/Ag
(110/50/20 [6wt%]/10/30/100/10 (nm))

ITO/TPD/CBZ2+Ir(ppy)$_3$/BCP/Alq$_3$/MgAg/Ag
(110/50/20 [6wt%]/10/30/100/10 (nm))

ITO/TPD/CBZ3+Ir(ppy)$_3$/BCP/Alq$_3$/MgAg/Ag
(110/50/20 [6wt%]/10/30/100/10 (nm))

ITO/TPD/CBZ3+Ir(ppy)$_3$/BCP/Alq$_3$/MgAg/Ag
(110/50/20 [6wt%]/10/30/100/10 (nm))

ITO/TPD/CBZ3+Ir(ppy)$_3$/BCP/Alq$_3$/MgAg/Ag
(110/50/20 [6wt%]/10/30/100/10 (nm))

ITO/TPD/CBZ4+Ir(ppy)$_3$/BCP/Alq$_3$/MgAg/Ag
(110/50/20 [6wt%]/10/30/100/10 (nm))

ITO/TPD/CBZ4+Ir(ppy)$_3$/BCP/Alq$_3$/MgAg/Ag
(110/50/20 [6wt%]/10/30/100/10 (nm))

ITO/TPD/CBZ4+Ir(ppy)$_3$/BCP/Alq$_3$/MgAg/Ag
(110/50/20 [6wt%]/10/30/100/10 (nm))

ITO/TPD/CBZ5+Ir(ppy)$_3$/BCP/Alq$_3$/MgAg/Ag
(110/50/20 [6wt%]/10/30/100/10 (nm))

ITO/TPD/CBZ5+Ir(ppy)$_3$/BCP/Alq$_3$/MgAg/Ag
(110/50/20 [6wt%]/10/30/100/10 (nm))

ITO/TPD/CBZ5+Ir(ppy)$_3$/BCP/Alq$_3$/MgAg/Ag
(110/50/20 [6wt%]/10/30/100/10 (nm))

ITO/TPD/CBZ6+Ir(ppy)$_3$/BCP/Alq$_3$/MgAg/Ag
(110/50/20 [6wt%]/10/30/100/10 (nm))

ITO/TPD/CBZ6+Ir (ppy)$_3$/BCP/Alq$_3$/MgAg/Ag
(110/50/20 [6wt%]/10/30/100/10 (nm))

ITO/TPD/CBZ6+Ir (ppy)$_3$/BCP/Alq$_3$/MgAg/Ag
(110/50/20 [6wt%]/10/30/100/10 (nm))

ITO/TPD/CBZ7+Ir(ppy)$_3$/BCP/Alq$_3$/MgAg/Ag
(110/50/20 [6wt%]/10/30/100/10 (nm))

ITO/TPD/CBZ7+Ir(ppy)$_3$/BCP/Alq$_3$/MgAg/Ag
(110/50/20 [6wt%]/10/30/100/10 (nm))

ITO/TPD/CBZ7+Ir(ppy)$_3$/BCP/Alq$_3$/MgAg/Ag
(110/50/20 [6wt%]/10/30/100/10 (nm))

ITO/TPD/CBZ8+Ir(ppy)$_3$/BCP/Alq$_3$/MgAg/Ag
(110/50/20 [6wt%]/10/30/100/10 (nm))

ITO/TPD/CBZ8+Ir(ppy)$_3$/BCP/Alq$_3$/MgAg/Ag
(110/50/20 [6wt%]/10/30/100/10 (nm))

ITO/TPD/CBZ8+Ir(ppy)$_3$/BCP/Alq$_3$/MgAg/Ag
(110/50/20 [6wt%]/10/30/100/10 (nm))

ITO/TPD/CBZ11+Ir(ppy)$_3$/BCP/Alq$_3$/MgAg/Ag
(110/50/20 [6wt%]/10/30/100/10 (nm))

ITO/TPD/CBZ12+Ir(ppy)$_3$/BCP/Alq$_3$/MgAg/Ag
(110/50/20 [6wt%]/10/30/100/10 (nm))

ITO/TPD/CBZ12+Ir(ppy)$_3$/BCP/Alq$_3$/MgAg/Ag
(110/50/20 [6wt%]/10/30/100/10 (nm))

ITO/TPD/CBZ12+Ir(ppy)$_3$/BCP/Alq$_3$/MgAg/Ag
(110/50/20 [6wt%]/10/30/100/10 (nm))

ITO/TPD/CBZ13+Ir(ppy)$_3$/BCP/Alq$_3$/MgAg/Ag
( 110/50/20 [ 6wt% ]/10/30/100/10 ( nm ))

ITO/TPD/CBZ14+Ir(ppy)$_3$/BCP/Alq$_3$/MgAg/Ag
( 110/50/20 [ 6wt% ]/10/30/100/10 ( nm ))

ITO/TPD/CBZ14+Ir(ppy)$_3$/BCP/Alq$_3$/MgAg/Ag
(110/50/20 [6wt%]/10/30/100/10 (nm))

ITO/TPD/CBZ14+Ir(ppy)$_3$/BCP/Alq$_3$/MgAg/Ag
(110/50/20 [6wt%]/10/30/100/10 (nm))

ITO/TPD/CBZ16+Ir(ppy)$_3$/BCP/Alq$_3$/MgAg/Ag
(110/50/20 [6wt%]/10/30/100/10 (nm))

ITO/TPD/CBZ16+Ir(ppy)$_3$/BCP/Alq$_3$/MgAg/Ag
(110/50/20 [6wt%]/10/30/100/10 (nm))

ITO/TPD/CBZ16+Ir(ppy)$_3$/BCP/Alq$_3$/MgAg/Ag
(110/50/20 [6wt%]/10/30/100/10 (nm))

ITO/TPD/CBZ19+Ir(ppy)$_3$/BCP/Alq$_3$/MgAg/Ag
(110/50/20 [6wt%]/10/30/100/10 (nm))

ITO/TPD/CBZ20+Ir(ppy)$_3$/BCP/Alq$_3$/MgAg/Ag
(110/50/20 [6wt%]/10/30/100/10 (nm))

ITO/TPD/CBZ20+Ir(ppy)$_3$/BCP/Alq$_3$/MgAg/Ag
(110/50/20 [6wt%]/10/30/100/10 (nm))

ITO/TPD/CBZ20+Ir(ppy)$_3$/BCP/Alq$_3$/MgAg/Ag
(110/50/20 [6wt%]/10/30/100/10 (nm))

ITO/TPD/CBZ21+Ir(ppy)$_3$/BCP/Alq$_3$/MgAg/Ag
(110/50/20 [6wt%]/10/30/100/10 (nm))

ITO/TPD/CBZ22+Ir(ppy)$_3$/BCP/Alq$_3$/MgAg/Ag
(110/50/20 [6wt%]/10/30/100/10 (nm))

ITO/TPD/CBZ22+Ir(ppy)$_3$/BCP/Alq$_3$/MgAg/Ag
(110/50/20 [6wt%]/10/30/100/10 (nm))

ITO/TPD/CBZ22+Ir (ppy)$_3$/BCP/Alq$_3$/MgAg/Ag
( 110/50/20 [ 6wt% ]/10/30/100/10 ( nm ))

ITO/TPD/CBZ24+Ir (ppy)$_3$/BCP/Alq$_3$/MgAg/Ag
( 110/50/20 [ 6wt% ]/10/30/100/10 ( nm ))

ITO/TPD/CBZ24+Ir(ppy)$_3$/BCP/Alq$_3$/MgAg/Ag
(110/50/20 [6wt%]/10/30/100/10 (nm))

ITO/TPD/CBZ24+Ir(ppy)$_3$/BCP/Alq$_3$/MgAg/Ag
(110/50/20 [6wt%]/10/30/100/10 (nm))

3,6-DIPHENYLCARBAZOLE COMPOUND AND ORGANIC ELECTROLUMINESCENT DEVICE

BACKGROUND OF THE INVENTION

1. Field of the Invention

The present invention relates to a carbazole compound and a new organic electroluminescent device. In particular, the present invention relates to a 3,6-diphenylcarbazole compound which realizes an organic electroluminescent device having high durability and high luminous efficiency and an organic electroluminescent device including the same. Further, the 3,6-diphenylcarbazole compound of the present invention can be applied to other fields such as photoelectric conversion devices and charge transporting materials for organic photosensitive elements.

2. Discussion of the Background

Organic thin film electroluminescent devices have been noted because of having the following advantages:
(1) viewing angle is wide, and visibility is high because the devices are a self-luminescent device; and
(2) space can be saved because the devices are a thin film type perfectly solid device.

Therefore, in recent years, research on commercialization thereof has been conducted. However, there are the following problems to be overcome at the present time:
(1) the energy conversion efficiency and the luminescent quantum efficiency have been further improved; and
(2) the stability of the organic thin film with time (i.e., durability of the device) has to be further improved.

Organic electroluminescent devices through the use of low-molecular materials and through the use of polymers have been reported up to now. With respect to the low-molecular material systems, -realization of increases in efficiency due to adoption of various laminated structures and an improvement of the durability by appropriately controlling a doping method have been reported. However, in the case of an aggregate of low molecular materials, it is reported that change in the state of film occurs with a long time and, therefore, there is an essential problem in the stability of the film.

In contrast, with respect to polymer based materials, researches have been intensely performed primarily on PPV (poly-p-phenylenevinylene)-based devices, poly-thiophene based devices, and the like. However, these systems have drawbacks in that it is difficult to increase the purity, and the fluorescent quantum yield is essentially low. Therefore, any high performance organic electroluminescent device has not been-produced under the present circumstances. In consideration that polymer materials in a glass state is essentially stable, an excellent organic electroluminescent device can be provided if a high fluorescent quantum yield can be imparted to the polymer materials. As described above, it is known that organic electroluminescent devices through the use of low-molecular materials and through the use of polymers have advantages as well as drawbacks.

Recently, research has also been intensely performed on the improvement of efficiency through the use of triplet excitons (refer to T. Tsutsui et al., Jpn. J. Appl. Phys. Vol. 38, L1502 (1999); and C. Adachi, M. A. Baldo, S. R. Forrest and M. E. Thompson, Appl. Phys. Lett., Vol. 77, 904 (2000), and the like), and it has been made clear that the luminous efficacy has been improved significantly. In addition, reports on host materials used for luminescent layers have been increased. Among them, typical examples of host materials include 4,4'-bis(carbazolyl-9)biphenyl (CBP) represented by the formula described below. However, it has been made clear from the following research that crystallization of CBP has proceeded in the luminescent layer, resulting in shortening of the life of the device (refer to WO01/72927 A1, for example).

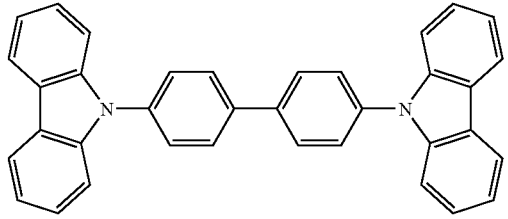

In attempting to avoid this problem, researches on carbazole compounds in place of CBP have been described in WO01/72927 A1, Japanese Unexamined Patent Application Publication No. 9-310066, and the like. Furthermore, researches on methods for synthesizing carbazole compounds and electrochemical behaviors of the carbazole compounds have also been performed (refers to M. Park et al., Tetrahedron 54 (1998) 12707 to 12714, W. Laum et al., Journal fuer Praktische Chemie (Leipzig) 317 (6) (1975) 995 to 1004, and the like). However, every compound described above does not have a desired durability and luminous efficiency.

SUMMARY OF THE INVENTION

The present invention has been made in consideration of the present circumstances of the above-described known technology. Accordingly, it is an object of the present invention to provide a new carbazole compound, which is a material for realizing an organic electroluminescent device having high durability and high luminous efficiency.

Another object of the present invention is to provide an organic electroluminescent device, which has high luminous efficiency and high durability.

Briefly these objects and other objects of the present invention as hereinafter will become more readily apparent can be attained by a 3,6-diphenylcarbazole compound (hereinafter referred to as a 3,6-diphenylcarbazole derivative) represented by the following formula (I):

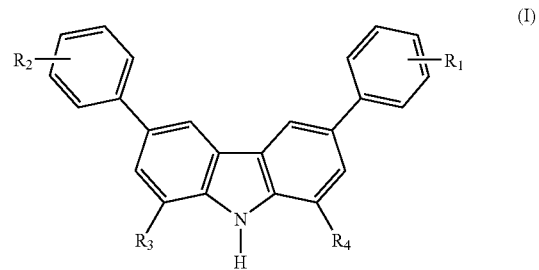

wherein $R_1$ and $R_2$ independently represent a hydrogen atom, a substituted or unsubstituted alkyl group, a substituted or unsubstituted alkoxy group, or an aryl group which may have a halogen atom or a substituent, and $R_3$ and $R_4$ independently represent a hydrogen atom, a substituted or unsubstituted alkyl group, or an aryl group which may have a substituent.

Alternatively the 3,6-diphenylcarbazole derivative may be a compound which is produced by a reaction of the 3,6-diphenylcarbazole derivative according to the above-described first aspect and a halogenated aryl and which is represented by the following formula (II):

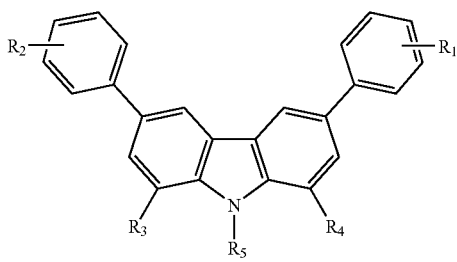

(II)

wherein $R_1$ and $R_2$ independently represent a hydrogen atom, a substituted or unsubstituted alkyl group, a substituted or unsubstituted alkoxy group, or an aryl group which may have a halogen atom or a substituent, $R_5$ represents a substituted or unsubstituted alkyl group or an aryl group which may have a substituent, and $R_3$ and $R_4$ independently represent a hydrogen atom, a substituted or unsubstituted alkyl group, or an aryl group which may have a substituent.

With respect to the 3,6-diphenylcarbazole derivative having formula (II), the derivative preferably has the following formula (III) or (VI):

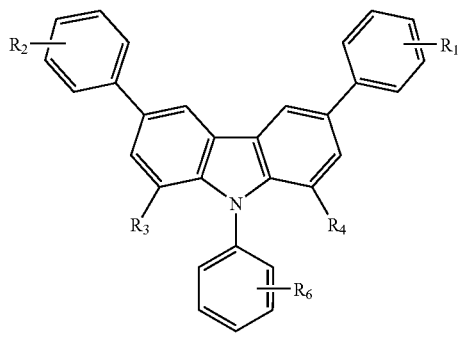

(III)

wherein $R_1$, $R_2$ and $R_6$ independently represent a hydrogen atom, a substituted or unsubstituted alkyl group, a substituted or unsubstituted alkoxy group, or an aryl group which may have a halogen atom or a substituent and $R_3$ and $R_4$ independently represent a hydrogen atom, a substituted or unsubstituted alkyl group, or an aryl group which may have a substituent; or

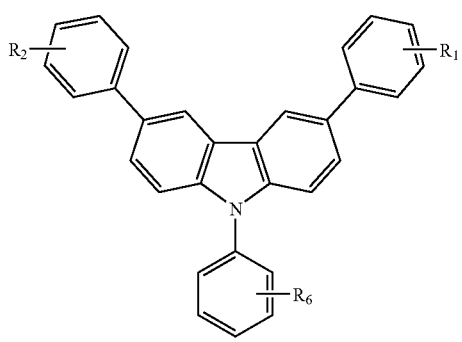

(IV)

wherein $R_1$, $R_2$ and $R_6$ independently represent a hydrogen atom, a substituted or unsubstituted alkyl group, a substituted or unsubstituted alkoxy group, or an aryl group which may have a halogen atom or a substituent.

Furthermore, as a result of the inventors' intensive research, it is found out that an organic electroluminescent device including an organic layer containing a 3,6-diphenylcarbazole derivative represented by formula (II) has an excellent electroluminescent property.

As the second aspect of the present invention, an organic electroluminescent device is provided which includes at least one layer including a luminescent layer formed between an anode and a cathode facing each other, wherein a 3,6-diphenylcarbazole derivative represented by the following formula (II) is contained in the at least one layer:

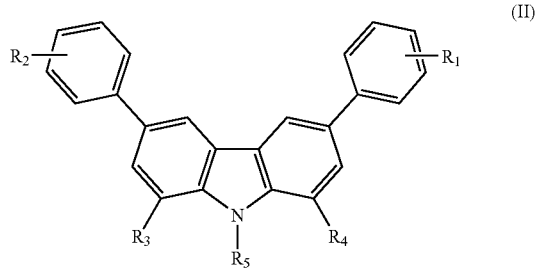

(II)

wherein $R_1$ and $R_2$ independently represent a hydrogen atom, a substituted or unsubstituted alkyl group, a substituted or unsubstituted alkoxy group, or an aryl group which may have a halogen atom or a substituent, $R_5$ represents a substituted or unsubstituted alkyl group or an aryl group which may have a substituent, and $R_3$ and $R_4$ independently represent a hydrogen atom, a substituted or unsubstituted alkyl group, or an aryl group which may have a substituent.

Alternatively, the at least one layer includes the luminescent layer and a hole transporting layer including a 3,6-diphenylcarbazole derivative represented by formula (II).

Alternatively, the luminescent layer includes a 3,6-diphenylcarbazole derivative represented by formula (II).

Alternatively, the at least one layer includes the luminescent layer and an electron transporting layer including a 3,6-diphenylcarbazole derivative represented by formula (II).

Alternatively, the at least one layer includes a hole transporting layer, the luminescent layer, and an electron transporting layer, wherein the luminescent layer includes a 3,6-diphenylcarbazole derivative represented by formula (II) which serves as a host material. The luminescent layer preferably includes an iridium complex as a guest material.

In electroluminescent device, it is known that carbazole compounds have both a hole transportability and an electron transferability (i.e., a bipolar property). The above-mentioned compound of the present invention has also the same property. By changing the substituents (electron accepting substituents or electron donating substituents) of the 3,6-diphenylcarbazole compound, the resultant compounds can also be used for the hole-transporting layer and the electron transporting layer.

When an organic electroluminescent device is energized, Joule heat is generated. The Joule heat causes not only advance of recrystallization, coagulation, and the like of organic layer but also diffusion of low-molecular materials; resulting in deterioration of the durability of the device. In contrast, in the organic electroluminescent device of the present invention, the 3,6-diphenylcarbazole derivative is used for the organic layer, and thereby the deterioration of the device due to recrystallization and coagulation and the deterioration of the device due to diffusion can be suppressed. Therefore, an electroluminescent device having high efficiency and excellent durability can be provided.

These and other objects, features and advantages of the present invention will become apparent upon consideration of the following description of the preferred embodiments of the present invention taken in conjunction with the accompanying drawings.

BRIEF DESCRIPTION OF THE DRAWINGS

Various other objects, features and attendant advantages of the present invention will be more fully appreciated as the same becomes better understood for the detailed description when considered in connection with the accompanying drawings in which like reference characters designate like corresponding parts throughout and wherein.

DETAILED DESCRIPTION OF THE INVENTION

Figure 1:
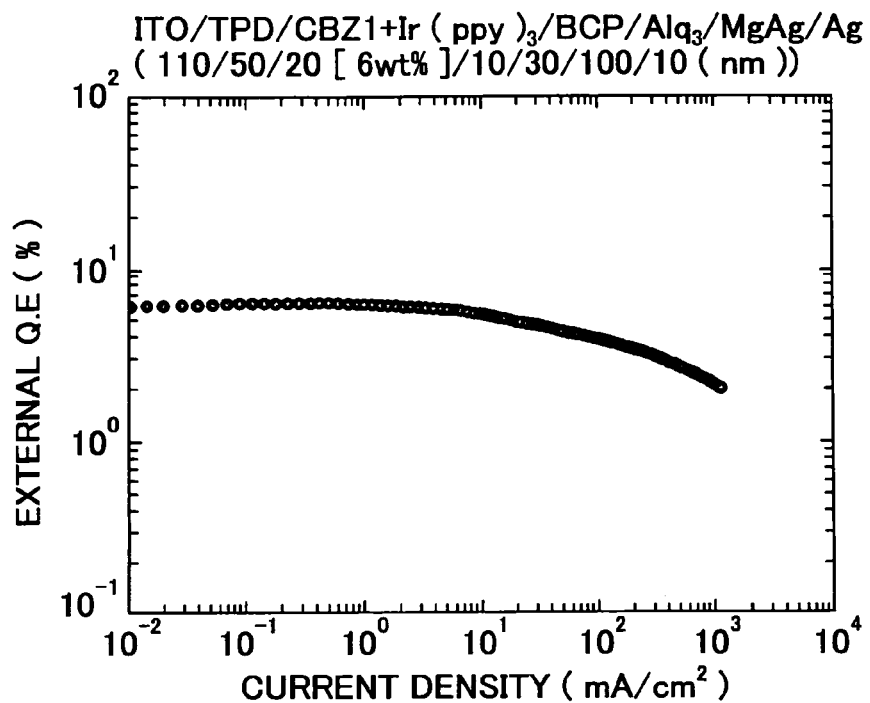
FIG. 1 is a graph showing the relationship between the current and the quantum efficiency of the organic electroluminescent device of Example 1.

A 3,6-diphenylcarbazole derivative of the present invention will be described below in further detail.

In the present invention, a 3,6-diphenyl-9H-carbazole derivative represented by formula (I) and a 3,6-diphenylcarbazole derivative represented by formula (II) may be produced by the following reaction.

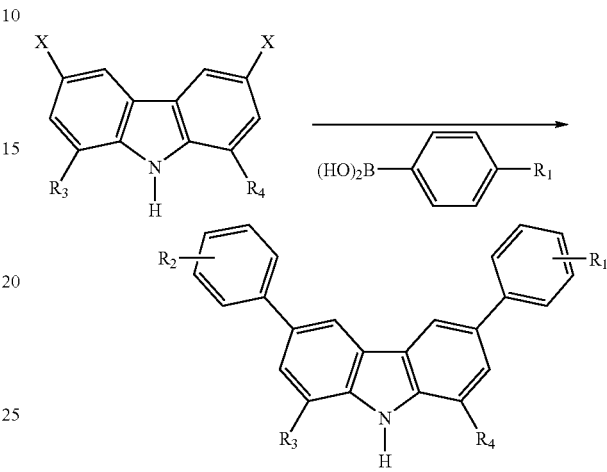

(wherein X represents a halogen atom, and $R_1=R_2$.)

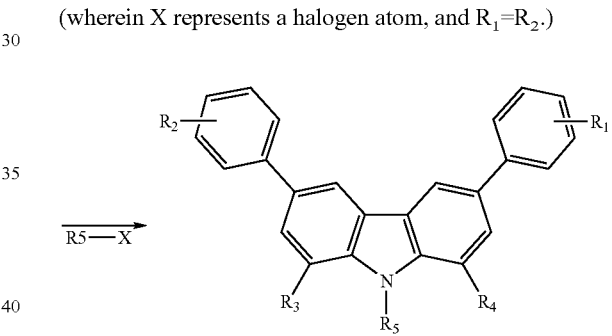

(wherein X represents a halogen atom.)

The 3,6-diaryl-9H-carbazole derivative in the first stage is produced by the Suzuki-Miyaura reaction which is known as a cross coupling reaction between an aryl boron compound and an organic halide in the presence of a palladium catalyst.

An aryl boronate ester, which is thermally stable and can be easily handled in air and which is synthesized from a halogenated aryl through the use of bis(pinacolato)diboron, may be used in place of the above-described aryl boronate.

Preferably, a halogen atom in the 3,6-dihalogeno-9H-carbazole derivative is an iodide or a bromide from the viewpoint of the reactivity.

Various catalysts, e.g., $Pd(PPh_3)_4$, $PdCl_2(PPh_3)_2$, $Pd(OAc)_2$, and $PdCl_{21}$ can be used as the palladium catalyst. Among these catalysts, $Pd(PPh_3)_4$ is typically used.

A base is indispensable to this reaction, and a relatively weak acid, e.g., $Na_2CO_3$ or $NaHCO_3$, yields an excellent result. In the case where the reaction is influenced by steric hindrance and the like, using a strong base, e.g., $Ba(OH)_2$ or $K_3PO_4$, is effective. In addition, sodium hydroxide, potassium hydroxide, metal alkoxides, e.g., potassium t-butoxide, sodium t-butoxide, lithium t-butoxide, potassium 2-methyl-2-butoxide, sodium 2-methyl-2-butoxide, sodium methoxide, sodium ethoxide, and potassium ethoxide, potassium methoxide, and the like can also be used. Organic bases, e.g., triethylamine, may also be used.

Specific examples of the reaction solvents include alcohols and ether-based solvents, e.g., methanol, ethanol, isopropanol, butanol, 2-methoxyethanol, and 1,2-dimethoxyethane, bis(2-methoxyethyl) ether; cyclic ether-based solvents, e.g., dioxane and tetrahydrofuran; and furthermore, benzene, toluene, xylene, dimethyl sulfoxide, N,N-dimethylformamide, N-methyl pyrrolidone, and 1,3-dimethyl-2-imidazolidinone.

The 3,6-diaryl-9H-carbazole derivative produced in the first stage is derived to a 3,6-diphenylcarbazole derivative of the present invention by the Ullmann reaction in the second stage.

Specific examples of the thus produced 3,6-diphenyl-9H-carbazole derivative represented by formula (I) and the 3,6-diphenylcarbazole derivative represented by formula (II) of the present invention will be described below.

In the case where $R_1$, $R_2$, $R_3$, $R_4$, and $R_5$ in the above-described formulae (I) and (II) independently represent a substituted or unsubstituted alkyl group, examples of the alkyl groups include straight-chain, branched chain, or circular alkyl groups having from 1 to 25 carbon atoms. These alkyl groups may further contain a fluorine atom, a cyano group, a phenyl group, or a phenyl group having a halogen atom or a straight-chain or branched chain alkyl group as a substituent. Specific examples of the substituted or unsubstituted alkyl groups include a methyl group, an ethyl group, a n-propyl group, an i-propyl group, a t-butyl group, s-butyl group, a n-butyl group, an i-butyl group, a pentyl group, a hexyl group, a heptyl group, an octyl group, a nonyl group, a decyl group, a 3,7-dimethyloctyl group, a 2-ethylhexyl group, a trifluoromethyl group, a 2-cyanoethyl group, a benzyl group, a 4-chlorobenzyl group, a 4-methylbenzyl group, a cyclopentyl group, and a cyclohexyl group.

In the case where $R_1$ and $R_2$ independently represent a substituted or unsubstituted alkoxy group, specific examples of the alkoxy groups include alkoxy groups in which an oxygen atom is inserted at the bonding position of the above-described substituted or unsubstituted alkyl groups.

In the case where $R_1$ and $R_2$ independently represent a halogen atom, examples thereof include a fluorine atom, a chlorine atom, and a bromine atom.

In the case where $R_1$, $R_2$, $R_3$, $R_4$, and $R_5$ in the above-described formulae (I) and (II) independently represent an aryl group which may have a substituent, specific examples of the aryl groups include a phenyl group, a naphthyl group, a biphenylyl group, a terphenylyl group, a pyrenyl group, a fluorenyl group, a 9,9-dimethyl-2-fluorenyl group, an azulenyl group, an anthryl group, a triphenylenyl group, a chrysenyl group, a fluorenylidenephenyl group, a 5H-dibenzo[a,d]cycloheptenylidenephenyl group, a furyl group, a benzofuranyl group, a carbazolyl group, a pyridyl group, a pyrrolidyl group, and an oxazolyl group. These may contain the above-described substituted or unsubstituted alkyl group, an alkoxy group, or a halogen atom, e.g., a fluorine atom, a chlorine atom, a bromine atom, or an iodine atom, as a substituent.

The 3,6-diphenylcarbazole derivative described above can be used for any of a hole transporting layer, a luminescent layer, and an electron transporting layer. It is well known that carbazole compounds have a bipolar property. Furthermore, the carbazole compounds can be applied to the hole transporting layer, the luminescent layer, and the electron transporting layer, as described above, through the molecular design of the carbazole compounds made for achieving the function required for the organic electroluminescent device.

Among the organic layers in the organic electroluminescent device of the present invention, the layer containing the above-described 3,6-diphenylcarbazole derivative can be formed by coating a coating liquid including the derivative and a known thermoplastic polymer using a known method, e.g., a spin coating method or a casting method. In addition to the wet type film forming methods, dry type film forming methods, e.g., a vapor deposition method and a sputtering method, may be used.

The organic layer constituting the organic electroluminescent device may be composed of a single organic layer or a plurality of organic layers. In the case where the organic layer is composed of a single layer, the layer may be composed of the 3,6-diphenylcarbazole derivative alone. In some cases, low-molecular compounds having an electron transporting property can be dispersed therein. In addition, a polymer or another electron transporting polymer can be blended with the derivative. Furthermore, the organic layer may be doped with a very small amount of fluorescent molecule having a very high fluorescent quantum efficiency. By using such methods, the efficiency can be improved. Known materials having an ability to transport an electron can be used as the electron transporting substance. For example, fluorenone, anthraquinodimethane, diphenoquinone, thiopyran dioxide, perylenetetracarboxylic acid, fluorenylidenemethane, anthrone, 2,9-dimethyl-4,7-diphenyl-1,10-phenanthroline (hereafter abbreviated as BCP), 2,9-diethyl-4,7-diphenyl-1, 10-phenanthroline, and the like and derivatives thereof, oxadiazole derivatives and triazole derivatives, which have an excellent electron transporting property according to known reports, may be used. Laser coloring materials and the like which shows a strong fluorescence in a solution state and known low-molecular fluorescent materials which have been used as luminescent materials in organic electroluminescent devices may be used as the fluorescent molecule having a very high fluorescent quantum efficiency. Specific examples of the materials include anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldadine, bisbenzoxazoline, bisstyryl, pyrazine, cyclopentadiene, quinoline metal complexes, aminoquinoline metal complexes, benzoquinoline metal complexes, imines, diphenylethylene, vinylanthracene, diaminocarbazole, pyran, thiopyran, polymethine, merocyanine, imidazole-chelated oxinoid compounds, quinacridone, rubrene, and the like and derivatives thereof. Among the above-described metal complexes, chelate metal complexes such as 8-hydroxyquinolinol aluminum complexes (hereafter abbreviated as Alq3) and their derivatives are preferably used because of having an excellent film forming property.

Furthermore, if necessary, the organic layer may be composed of a plurality of layers. In the case where a 3,6-diphenylcarbazole derivative-containing layer is used as a hole injection and transporting layer, an electron injection and transporting layer, a luminescent layer, and the like may be further overlaid thereon by a spin coating method or a vapor deposition method. Alternatively, it is effective for improving the performance to form a hole injection and transporting layer in advance of formation of the 3,6-diphenylcarbazole derivative-containing layer. Known materials, e.g., phthalocyanine-based compounds, porphyrin-based compounds, oxadiazole, triazole, triphenylamine-based compounds, and polysilanes, which perform functions in organic electroluminescent devices according to known reports, may be used as the material constituting the hole injection and transporting layer. Among the compounds, examples of preferable tertiary amine compounds typified by triphenylamine include N,N'-di-m-tolyl-N,N'-diphenyl-4,4'-diphenyldiamine (hereafter abbreviated as TPD) and N,N'-di-1-naphthyl-N,N'-diphenyl-4,4'-diphenyldiamine (hereafter abbreviated as NPD). In the case where the 3,6-diphenylcarbazole derivative-containing layer is used as an electron injection and transporting layer, a hole injection and transporting layer, a luminescent layer, and the like may be further overlaid thereon by a spin coating method or a vapor deposition method.

It is also very useful that the 3,6-diphenylcarbazole derivative is used as a host material in the luminescent layer. The triplet exciton state of the 3,6-diphenylcarbazole derivative can be used effectively in combination with a phosphorescent dopant.

Preferably, the phosphorescent dopant is a metal complex which includes a phenylpyridine skeleton as a ligand and which contains at least one metal selected from the group consisting of Ir, Ru, Pd, Pt, Os, and Re. Specific examples of the phosphorescent dopant include tris(2-phenylpyridine)iridium (hereafter referred to as Ir(ppy)$_3$) and tris(2-phenylpyridine)ruthenium.

In the case where the 3,6-diphenylcarbazole derivative of the present invention is used as the host material, preferably, the phosphorescent dopant is 0.1 to 25 percent by weight relative to the 3,6-diphenylcarbazole derivative.

The film thickness of the thus formed organic layer is not specifically limited, and is generally within the range of 5 nm to 20 μm. More preferably, the film thickness is within the range of 5 nm to 0.2 μm. The film thickness is determined in consideration of occurrence of film defects, e.g., a pinhole, the interference of light in the device at a luminescent wavelength, an increase in the applied voltage due to an increase in the film thickness, and the like matters.

In the present invention, metals, alloys, metal oxides, and the like, which have work functions larger than 4 eV, and preferably larger than 4.8 eV, are used as an anode of the organic electroluminescent device. Specific examples of such an electrode material include gold, platinum, palladium, silver, tungsten, nickel, cobalt, and the use of transparent electrodes made of ITO, CuI, SnO$_2$, ZnO, and the like. In particular, an ITO substrate is preferably used. Preferably, the ITO substrate has a smooth surface, and therefore the substrate is used after dirt on the surface is cleaned thoroughly. Known methods are adopted as the cleaning method. However, ultraviolet irradiation in an ozone atmosphere or a plasma treatment in an oxygen atmosphere is preferable.

On the other hand, metals, alloys, and the like, which have work functions smaller than 4 eV, are used as a cathode. Specific examples of such a substance include cesium, sodium, calcium, magnesium, lithium, aluminum, samarium, and alloys thereof.

In the case where the organic electroluminescent device is used as a surface-emitting device, it is desirable that at least one of these electrodes is adequately transparent in the luminescent wavelength region of the device, and the other side has adequately large reflectance in the luminescent wavelength region. In the case of edge-emitting device, it is not necessary for the electrodes to be transparent. Preferably, the transparent electrode is the above-described ITO, and a transparent glass plate or plastic plate is used as the substrate thereof.

In order to improve the stability of the resulting organic electroluminescent device to withstand environmental conditions such as temperature, moisture, and atmosphere of the environment, it is effective to dispose a protective layer on the surface of the device or to protect the entire device by sealing with a nitride film or the like.

When a voltage is applied to the thus produced organic electroluminescent device of the present invention while the anode is connected to the plus side, and the cathode is connected to the minus side, electroluminescence can be observed.

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Manufacturing Example 1

Figure 58:
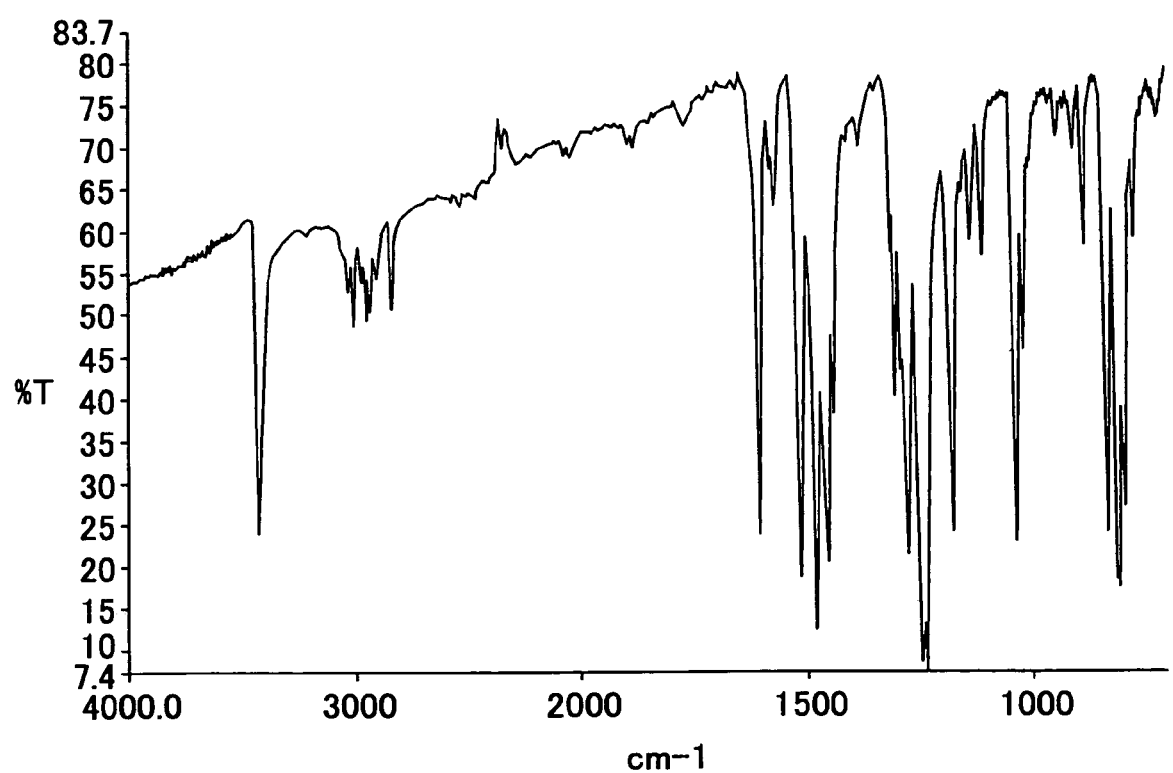
FIG. 58 is a diagram showing an infrared absorption spectrum (KBr pellet method) of 3,6-bis(4-methoxyphenyl)carbazole produced in Manufacturing Example 1.

A solution was prepared by adding 20.0 g of 3,6-dibromocarbazole, 20.6 g of 4-methoxyphenylboronic acid, and 2.23 g of tetrakis(triphenylphosphine)palladium into 60 ml of ethanol and 250 ml of toluene. The resulting solution was blended with 120 ml of a 22% aqueous solution of sodium carbonate, and the mixture was heated under reflux in a nitrogen atmosphere for 5.5 hours. Insoluble materials were removed therefrom by performing hot filtration using a filter aid. Thereafter, the organic layer was separated from the aqueous layer, and the solvent was distilled off under a reduced pressure. After washing with water and drying were performed, 20.2 g of a light brown powder was prepared. The resulting powder was recrystallized in a mixed solvent of toluene/ethanol and, thereby, 13.5 g of a colorless needle crystal of 3,6-bis(4-methoxyphenyl)carbazole was produced. The physical properties thereof were as follows.

melting point: 213.0° C. to 214.0° C.
elemental analysis value (%):
measured value/calculated value
C, 82.69/82.30; H, 5.61/5.58; N, 3.70/3.69;
The infrared absorption spectrum (KBr pellet method) thereof is shown in FIG. 58.
NH stretching vibration: 3426 cm$^{-1}$
COC stretching vibration: 1235, 1035 cm$^{-1}$ Manufacturing Example 2

Figure 59:
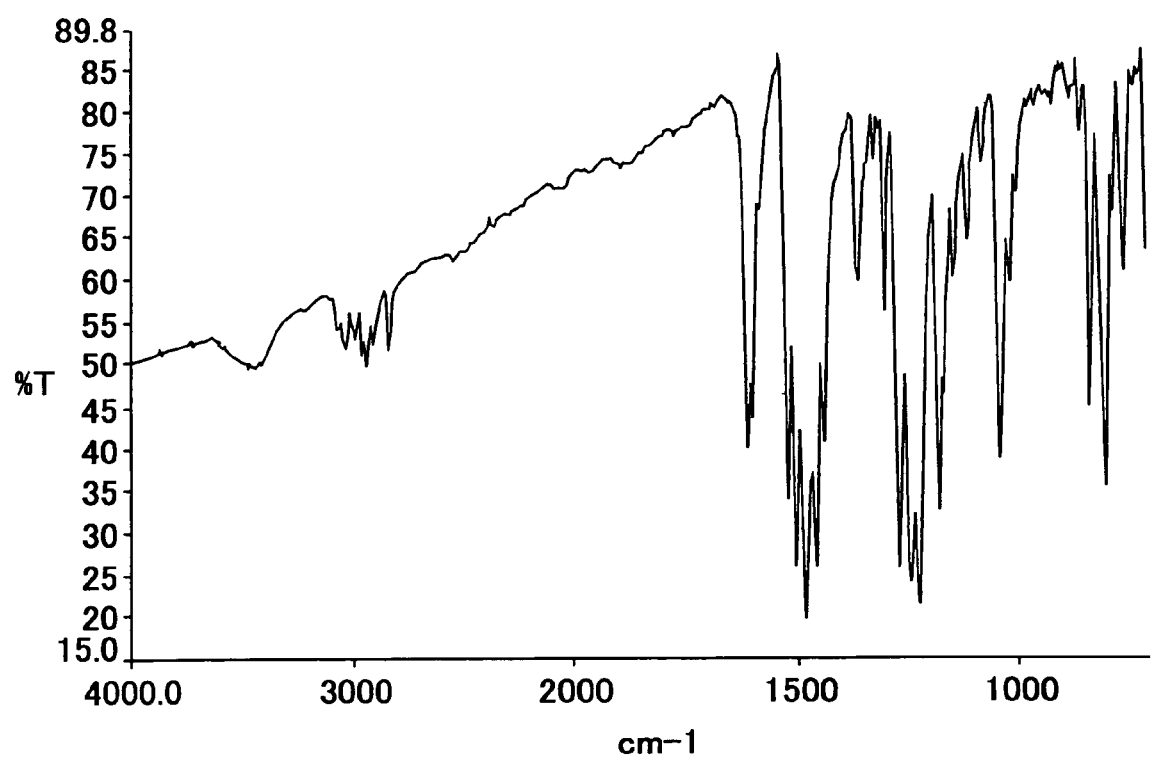
FIG. 59 is a diagram showing an infrared absorption spectrum (KBr pellet method) of 3,6-bis(4-methoxyphenyl)-9-phenylcarbazole produced in Manufacturing Example 2.

A solution was prepared by mixing 13.4 g of 3,6-bis(4-methoxyphenyl)carbazole, 40 ml of iodobenzene, 19.3 g of potassium carbonate, and 1.0 g of copper powder, and heating the mixture under reflux in a nitrogen atmosphere for 3 hours. After cooling was performed to 100° C., toluene was added thereto, and insoluble materials were removed therefrom using a filter aid. The solvent was distilled off under a reduced pressure and, thereafter, washing was performed with methanol. As a result, 14.8 g of a colorless needle crystal of 3,6-bis(4-methoxyphenyl)-9-phenylcarbazole (referred to as CBZ1) was produced. The melting point thereof was as follows.

melting point: 169.5° C. to 170.5° C.
The resulting crystal was recrystallized in a mixed solvent of toluene/ethanol, and thereby a colorless needle crystal was produced. The physical properties thereof were as follows.
melting point: 170.0° C. to 171.0° C.
elemental analysis value (%):
measured value/calculated value
C, 84.31/84.37; H, 5.44/5.53; N, 3.06/3.07;

An infrared absorption spectrum (KBr pellet method) is shown in FIG. 59.

Manufacturing Examples 3 to 7

3,6-Diphenylcarbazole derivatives of the present invention shown in Table 1 were produced in the same manner as in Manufacturing Example 2 except that iodine compounds suitable for producing compounds shown in Table 1 were used in place of iodobenzene in Manufacturing Example 2. The analytical results are also shown in Table 1.

Manufacturing Example 8

A solution was prepared by adding 12.7 g of 3,6-dibromocarbazole, 10.0 g of phenylboronic acid, and 2.61 g of tetrakis(triphenylphosphine)palladium into 40 ml of ethanol and 170 ml of toluene. The resulting solution was blended with 90 ml of a 22% aqueous solution of sodium carbonate, and the mixture was heated under reflux in a nitrogen atmosphere for 5 hours. Insoluble materials were removed therefrom by performing hot filtration using a filter aid. Thereafter, the organic layer was separated from the aqueous layer, and the solvent was distilled off under a reduced pressure. After washing with water and drying were performed, a light brown powder was prepared. The resulting powder was subjected to a column chromatography treatment (eluant: toluene), followed by washing with hexane. Thus, 6.0 g of a colorless needle crystal of 3,6-diphenylcarbazole was produced. The physical properties thereof were as follows.
  melting point: 180.5° C. to 181.5° C.
  elemental analysis value (%):
  measured value/calculated value
  C, 90.44/90.24; H, 5.25/5.38;N, 4.31/4.39;
  infrared absorption spectrum (KBr pellet method)
  NH stretching vibration: 3423, 3378 $cm^{-1}$ Manufacturing Examples 9 to 13

3,6-Diphenyl-9H-carbazole derivatives shown in Table 2 were produced in the same manner as in Manufacturing Example 8 except that arylboronic acids suitable for producing compounds shown in Table 2 were used in place of phenylboronic acid used in Manufacturing Example 8.

Manufacturing Examples 14 to 19

3,6-Diphenylcarbazole derivatives of the present invention shown in Table 1 were produced in the same manner as in Manufacturing Example 2 by the use of the 3,6-diphenyl-9H-carbazole derivatives produced in Manufacturing Examples 8 to 13 and iodobenzene. The analytical results are also shown in Table 1.

Manufacturing Example 20

A solution was prepared by mixing 1.62 g of 3,6-bis(biphenylyl-4)carbazole produced in Manufacturing Example 13, 1.43 g of 4-iodobiphenyl, 1.90 g of potassium carbonate, and 0.20 g of a copper powder, in 20 ml of nitrobenzene, and heating the mixture under reflux in a nitrogen atmosphere for 3 hours. After cooling was performed to 100° C., insoluble materials were removed therefrom using a filter aid. The solvent was distilled off under a reduced pressure, and the resultant product was washed with methanol, followed by recrystallization in a mixed solvent of toluene/ethanol. Thus, 0.90 g of a colorless needle crystal of 3,6,9-tris(biphenylyl-4)carbazole as shown in Table 1 was produced. The analytical results are also shown in Table 1.

Manufacturing Example 21

A solution was prepared by mixing 2.0 g of 3,6-diphenylcarbazole produced in Manufacturing Example 8, 0.26 g of sodium carbonate, and 200 ml of dehydrated acetone. Subsequently, 0.89 ml of diethyl sulfate was added dropwise to the resulting solution over 30 minutes at room temperature. After agitation was performed at room temperature for one day, the contents were poured into water, and extraction was performed using ethyl acetate. The organic layer thereof was washed with a sodium hydrogen carbonate aqueous solution. Thereafter, washing with water and drying were performed, and the solvent was distilled off. Thus a colorless powder was prepared. Recrystallization was performed in a mixed solvent of toluene/ethanol and, thereby, 1.70 g of a colorless plate crystal of 3,6-diphenyl-9-ethylcarbazole as shown in Table 1 was produced. The analytical results are also shown in Table 1.

Manufacturing Example 22

A colorless plate crystal of 3,6-bis(4-methoxyphenyl)-9-ethylcarbazole as shown in Table 1 was produced in the same manner as in Manufacturing Example 21 except that 3,6-bis (4-methoxyphenyl)carbazole produced in Manufacturing Example 1 was used in place of 3,6-diphenylcarbazole used in Manufacturing example 21. The analytical results are also shown in Table 1.

Manufacturing Example 23

A solution was prepared by adding 11.30 g of 3,6-dibromocarbazole, 10.40 g of 2-methylphenylboronic acid, and 1.27 g of tetrakis(triphenylphosphine)palladium into 30 ml of ethanol and 125 ml of toluene. The resulting solution was blended with 75 g of a 22% aqueous solution of sodium carbonate, and the mixture was heated under reflux in a nitrogen atmosphere for 4 hours. Insoluble materials were removed therefrom by hot filtration using a filter aid. Thereafter, the organic layer was separated from the aqueous layer, and the solvent was distilled off under a reduced pressure. Then washing with water and drying were performed. As a result, a light brown powder was prepared. The resulting powder was then subjected to a silica gel column chromatography treatment (eluant: toluene/hexane=1/1 on a volume ratio basis). Thus, 7.44 g of a colorless needle crystal of 3,6-bis(2-methylphenyl)carbazole was produced. The physical properties thereof were as follows.
  melting point:—(glassy state)
  elemental analysis value (%):
  measured value/calculated value
  C, 89.62/89.88; H, 6.00/6.09; N, 4.00/4.03;
  infrared absorption spectrum (KBr pellet method)
  NH stretching vibration: 3411 $cm^{-1}$ Manufacturing Example 24

A solution was prepared by mixing 3.41 g of 3,6-bis(2-methylphenyl)carbazole, 15 ml of o-iodobenzene, 5.51 g of potassium carbonate, and 0.5 g of copper powder, and heating the mixture under reflux in a nitrogen atmosphere for 3 hours. After cooling was performed to room temperature, toluene was added thereto, and insoluble materials were removed therefrom using a filter aid. The solvent was distilled off under a reduced pressure and, thereafter, a silica gel column chromatography treatment (eluant: toluene/hexane=1/8 on a volume ratio basis) was performed. As a result, 3.60 g of a colorless needle crystal of 3,6,9-tris(2-methylphenyl)carbazole as shown in Table 1 was produced. The analytical results are also shown in Table 1.

Manufacturing Example 25

3,6-Bis(2-methylphenyl)-9-phenylcarbazole of the present invention as shown in Table 1 was produced in the same manner as in Manufacturing Example 24 except that iodobenzene was used in place of o-iodobenzene in Manufacturing Example 24. The analytical results are also shown in Table 1.

Manufacturing Example 26

A solution was prepared by adding 10.00 g of 3,6-dibromocarbazole, 9.86 g of 3-fluorophenylboronic acid, and 1.08 g of tetrakis(triphenylphosphine)palladium into 30 ml of ethanol and 125 ml of toluene. The resulting solution was blended with 60 g of a 21.2% aqueous solution of sodium carbonate, and the mixture was heated under reflux in a nitrogen atmosphere for 5 hours. After the mixture was cooled to room temperature, insoluble materials were removed therefrom using a filter aid. Subsequently, the organic layer was separated from the aqueous layer, and the solvent was distilled off under a reduced pressure. After washing with water and drying were performed, a light brown powder was prepared. The resulting powder was subjected to an adsorption treatment by the use of silica gel, followed by recrystallization in a mixed solvent of ether/hexane. Thus, 4.07 g of a colorless needle crystal of 3,6-bis(3-fluorophenyl)carbazole was produced.
melting point: 151.5° C. to 152.5° C.
elemental analysis value (%):
measured value/calculated value
C, 81.00/81.11; H, 4.26/4.25; N, 4.00/3.94;
infrared absorption spectrum (KBr pellet method)
NH stretching vibration: 3392 cm$^{-1}$ Manufacturing Example 27

A solution was prepared by mixing 3.50 g of 3,6-bis(3-fluorophenyl)carbazole, 30 ml of iodobenzene, 5.00 g of potassium carbonate, and 0.25 g of a copper powder, and heating the mixture under reflux in a nitrogen atmosphere for 1.5 hours. After the mixture was cooled to 100° C., toluene was added thereto, and insoluble materials were removed therefrom using a filter aid. The solvent was distilled off under a reduced pressure. Subsequently, a silica gel column chromatography treatment (eluant: toluene) was performed, and recrystallization was performed in ethanol. Thus, a colorless needle crystal of 3,6-bis(3-fluorophenyl)-9-phenylcarbazole as shown in Table 1 was produced. The analytical results are also shown in Table 1.

Manufacturing Example 28

A light brown crude substance was produced in the same manner as in Manufacturing Example 2 except that 2-iodotoluene was used in place of iodobenzene in Manufacturing Example 2. The resulting crude substance was subjected to a silica gel column chromatography treatment (eluant: toluene), followed by recrystallization in toluene/ethanol. Thus, a colorless needle crystal of 3,6-bis(4-methoxyphenyl)-9-(2-methylphenyl)carbazole as shown in Table 1 was produced. The analytical results are also shown in Table 1.

Manufacturing Example 29

A solution was prepared by adding 6.50 g of 3,6-dibromocarbazole, 10.00 g of biphenyl-2-boronic acid, and 0.72 g of tetrakis(triphenylphosphine)palladium into 20 ml of ethanol and 100 ml of toluene. The resulting solution was blended with 40.g of a 22% aqueous solution of sodium carbonate, and the mixture was heated under reflux in a nitrogen atmosphere for 7.5 hours. After the mixture was cooled, toluene and water were added thereto, and insoluble materials were removed therefrom using a filter aid. Subsequently, the organic layer was separated from the aqueous layer, and the solvent was distilled off under a reduced pressure. After washing with water and drying were performed, so that a light brown powder was prepared. The resulting powder was subjected to a silica gel column chromatography treatment (eluant: toluene/hexane=2/1 on a volume ratio basis), followed by washing with ethanol. Thus, 5.22 g of a colorless needle crystal of 3,6-bis(2-biphenylyl)carbazole was produced. The physical properties thereof were as follows.
melting point: 186.0C to 189.0° C.
elemental analysis value (%)
measured value/calculated value
C, 91.46/91.69; H, 5.13/5.34; N, 3.05/2.97;
infrared absorption spectrum (KBr pellet-method)
NH stretching vibration: 3425 cm$^{-1}$ Manufacturing Example 30

A solution was prepared by mixing 3.00 g of 3,6-bis(2-biphenylyl)carbazole, 30 ml of o-iodobenzene, 3.70 g of potassium carbonate, and 0.5 g of a copper powder, and heating the mixture under reflux in a nitrogen atmosphere for 4 hours. After the mixture was cooled to room temperature, toluene was added thereto, and insoluble materials were removed therefrom using a filter aid. The solvent was distilled off under a reduced pressure and, thereafter, the deposited crystals were washed with ethanol, followed by recrystallization in a mixed solvent of toluene/ethanol. Thus, 2.60 g of a colorless needle crystal of 3,6-bis(2-biphenylyl)-9-phenylcarbazole as shown in Table 1 was produced. The analytical results are also shown in Table 1.

Manufacturing Example 31

A solution was prepared by adding 5.27 g of 3,6-dibromocarbazole, 11.3 g of 3-(4,4,5,5-tetramethyl-1,3 2-dioxaborolan-2-yl)biphenyl, and 0.58 g of tetrakis(triphenylphosphine)palladium into 16 ml of ethanol and 80 ml of toluene. The resulting solution was blended with 33 g of a 21.2% aqueous solution of sodium carbonate, and the mixture was heated under reflux in a nitrogen atmosphere for 8 hours. After the mixture was cool to room temperature, toluene was added thereto, and insoluble materials were removed therefrom using a filter aid. Subsequently, the organic layer was separated from the aqueous layer, and the solvent was distilled off under a reduced pressure. The resulting product was subjected to a silica gel column chromatography treatment (eluant: toluene/hexane=2/1 on a volume ratio basis), followed by washing with ethanol. Thus, 4.70 g of a colorless needle crystal of 3,6-bis(3-biphenylyl)carbazole was produced. The physical properties thereof were as follows.
melting point: 262° C.
elemental analysis value (%)

measured value/calculated value
C, 91.94/91.69; H, 5.15/5.34; N, 3.01/2.97;
infrared absorption spectrum (KBr pellet method)
NH stretching vibration: 3394 cm$^{-1}$ Manufacturing Example 32

A solution was prepared by mixing 4.20 g of 3,6-bis(3-biphenylyl)carbazole, 40 ml of iodobenzene, 5.20 g of potassium carbonate, and 0.70 g of copper powder, and heating the mixture under reflux in a nitrogen atmosphere for 3 hours. After the solution was cooled to room temperature, toluene was added thereto, and insoluble materials were removed therefrom using a filter aid. The solvent was distilled off under a reduced pressure, and thereafter the deposited crystals were washed with ethanol, followed by recrystallization in a mixed solvent of toluene/hexane. Thus, 3.65 g of a colorless plate crystal of 3,6-bis(3-biphenylyl)-9-phenylcarbazole as shown in Table 1 was produced. The analytical results are also shown in Table 1.

TABLE 1

| Manufacturing example No. | CBZ No. | $R_1$ | $R_2$ | $R_3$ | $R_4$ | $R_5$ | Melting point (° C.) | Element analysis (%) observed (calculated) | | |
|---|---|---|---|---|---|---|---|---|---|---|
| | | | | | | | | C | H | N |
| 3 | CBZ2 | 4-OCH$_3$ | 4-OCH$_3$ | H | H | 4-methylphenyl | 204.0 to 204.5 | 84.41 (84.41) | 5.75 (5.80) | 2.55 (2.98) |
| 4 | CBZ3 | 4-OCH$_3$ | 4-OCH$_3$ | H | H | 3-methylphenyl | 197.0 to 197.5 | 83.94 (84.40) | 5.72 (5.81) | 2.82 (2.98) |
| 5 | CBZ4 | 4-OCH$_3$ | 4-OCH$_3$ | H | H | 4-biphenylyl | 238.5 to 239.5 | 86.00 (85.85) | 5.42 (5.50) | 2.22 (2.63) |
| 6 | CBZ13 | 4-OCH$_3$ | 4-OCH$_3$ | H | H | 4-methoxyphenyl | 203.5 to 205.0 | 81.97 (81.63) | 5.51 (5.60) | 2.90 (2.88) |
| 7 | CBZ14 | 4-OCH$_3$ | 4-OCH$_3$ | H | H | 3-methoxyphenyl | 175.5 to 176.5 | 81.75 (81.63) | 5.81 (5.95) | 3.31 (3.34) |
| 14 | CBZ12 | H | H | H | H | phenyl | 106.5 to 108.5 | 91.50 (91.10) | 5.22 (5.36) | 3.37 (3.54) |
| 15 | CBZ5 | 4-CH$_3$ | 4-CH$_3$ | H | H | phenyl | 162.5 to 163.5 | 90.82 (90.74) | 5.85 (5.95) | 3.28 (3.31) |
| 16 | CBZ6 | 3-CH$_3$ | 3-CH$_3$ | H | H | phenyl | 133.5 to 135.0 | 90.87 (90.74) | 5.81 (5.95) | 3.34 (3.31) |
| 17 | CBZ7 | 3-OCH$_3$ | 3-OCH$_3$ | H | H | phenyl | glassy | 84.62 (84.37) | 5.44 (5.53) | 3.01 (3.07) |
| 18 | CBZ8 | 3-Cl | 3-Cl | H | H | phenyl | 156.5 to 158.0 | 78.01 (77.59) | 3.91 (4.12) | 2.97 (3.02) |
| 19 | CBZ16 | 4-phenyl | 4-phenyl | H | H | phenyl | 236.0 to 237.5 | 92.21 (92.11) | 5.25 (5.34) | 2.30 (2.56) |
| 20 | CBZ20 | 4-phenyl | 4-phenyl | H | H | 4-biphenylyl | 273.5 to 275.0 | 92.72 (92.42) | 5.10 (5.33) | 2.22 (2.25) |
| 21 | CBZ11 | H | H | H | H | C$_2$H$_5$ | 184.5 to 185.0 | 89.86 (89.86) | 6.03 (6.10) | 3.97 (4.03) |
| 22 | CBZ19 | 4-OCH$_3$ | 4-OCH$_3$ | H | H | C$_2$H$_5$ | 226.5 to 227.5 | 82.95 (82.53) | 6.22 (6.18) | 3.48 (3.44) |
| 24 | CBZ22 | 2-CH$_3$ | 2-CH$_3$ | H | H | 2-methylphenyl | 80.0 to 82.0 | 90.84 (90.58) | 6.26 (6.22) | 3.12 (3.20) |
| 25 | CBZ21 | 2-CH$_3$ | 2-CH$_3$ | H | H | phenyl | 121.0 to 122.0 | 90.84 (90.74) | 6.03 (5.95) | 3.19 (3.31) |
| 27 | CBZ23 | 3-F | 3-F | H | H | phenyl | 124.5 to 125.5 | 83.26 (83.51) | 4.22 (4.44) | 3.12 (3.25) |
| 28 | CBZ24 | 4-OCH$_3$ | 4-OCH$_3$ | H | H | 2-methylphenyl | 175.5 to 176.5 | 84.22 (84.41) | 5.84 (5.80) | 3.00 (2.98) |
| 30 | CBZ25 | 2-phenyl | 2-phenyl | H | H | phenyl | 233 | 92.57 (92.11) | 5.26 (5.34) | 2.57 (2.56) |
| 32 | CBZ26 | 3-phenyl | 3-phenyl | H | H | phenyl | 188.0 to 189.0 | 92.55 (92.11) | 5.21 (5.34) | 2.59 (2.56) |

TABLE 2

| Manufacturing example No. | 3,6-diphenyl-9H-carbazole derivative | Melting point (° C.) | Infrared absorption spectrum (KBr pellet method) NH stretching vibration (cm$^{-1}$) |
|---|---|---|---|
| 9 | (3,6-bis(4-methylphenyl)-9H-carbazole) | 199.0 to 200.5 | 3393 |
| 10 | (3,6-bis(3-methylphenyl)-9H-carbazole) | 165.0 to 166.5 | 3428 |
| 11 | (3,6-bis(3-methoxyphenyl)-9H-carbazole) | 150.0 to 151.0 | 3427 |
| 12 | (3,6-bis(3-chlorophenyl)-9H-carbazole) | 204.0 to 206.0 | 3308 |

TABLE 2-continued

| Manufacturing example No. | 3,6-diphenyl-9H-carbazole derivative | Melting point (° C.) | Infrared absorption spectrum (KBr pellet method) NH stretching vibration (cm$^{-1}$) |
|---|---|---|---|
| 13 | | 273.0 | 3392 |

EXAMPLE 1

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of $10^{-4}$ Pa to form a hole transporting layer with a thickness of 50 nm on the substrate. Subsequently, CBZ1 and Ir(ppy)$_3$ were co-deposited to from a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 1 and the maximum quantum efficiency is 6.6%.

Figure 2:
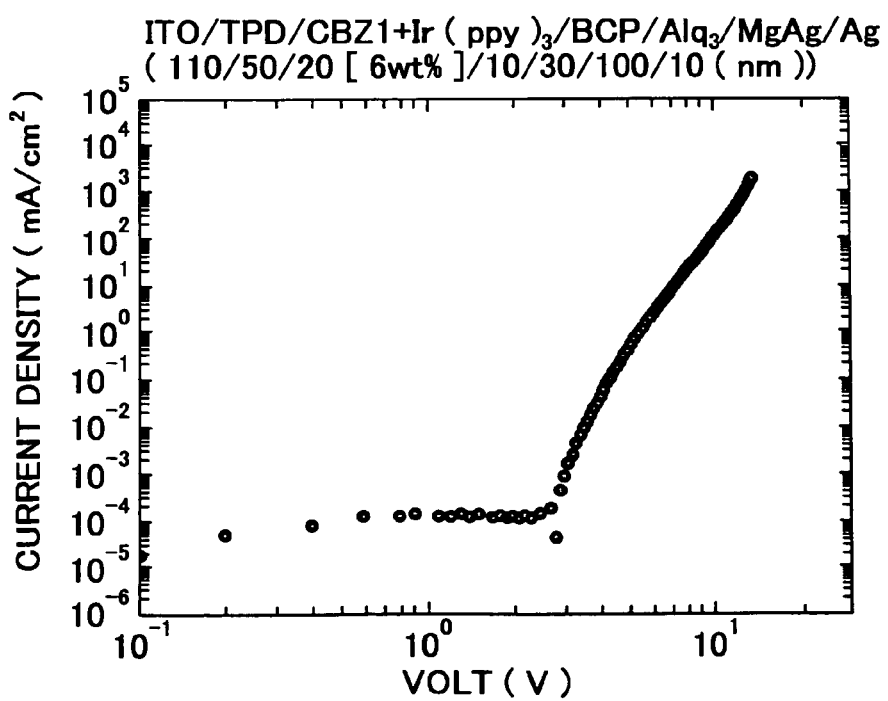
FIG. 2 is a graph showing the relationship between the current and the voltage of the organic electroluminescent device of Example 1.
Figure 3:
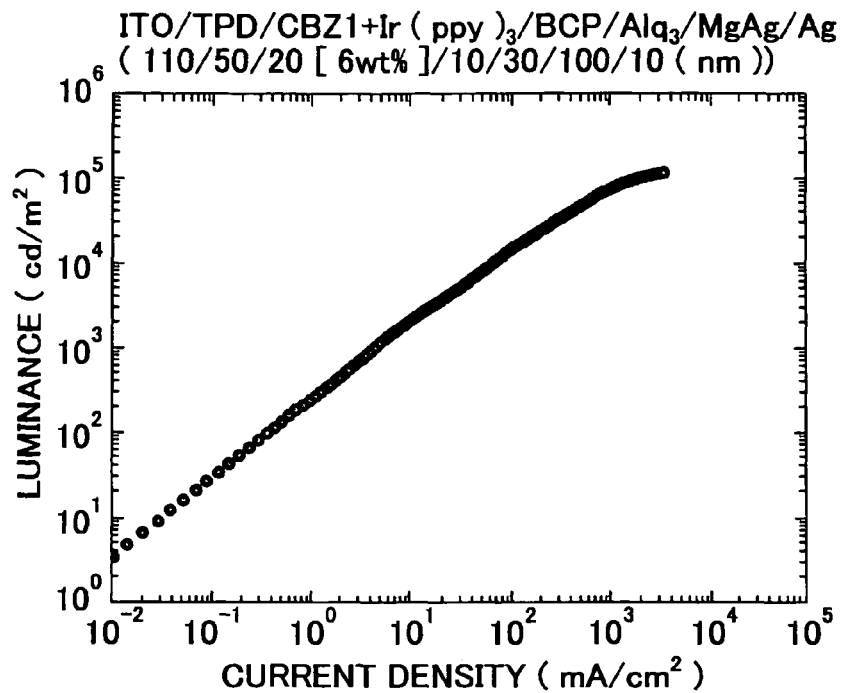
FIG. 3 is a graph showing the relationship between the current and the luminance of the organic electroluminescent device of Example 1.

In addition, the device has an excellent current-voltage characteristic as shown in FIG. 2. Namely the maximum current density was 4.065 A/cm$^2$ and the maximum luminance was 122,264 cd/m$^2$ (FIG. 3) when the applied voltage is 14.4 V. In addition, light having an emission spectrum such that a peak is observed at 510 nm was emitted from Ir(ppy)$_3$.

EXAMPLE 2

Figure 4:
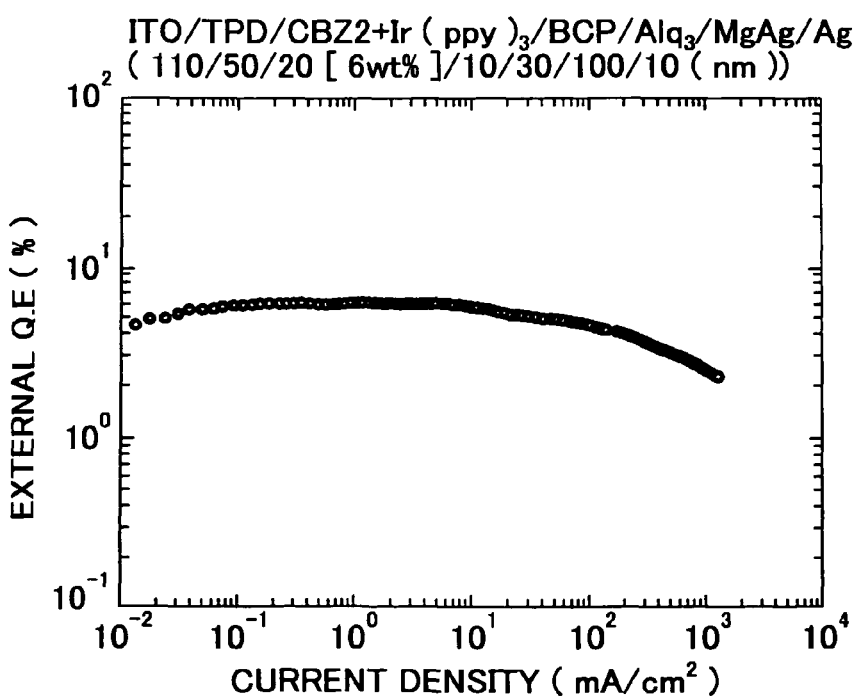
FIG. 4 is a graph showing the relationship between the current and the quantum efficiency of the organic electroluminescent device of Example 2.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of $10^{-4}$ Pa to form a hole transporting layer with a thickness of 50 nm on the substrate. Subsequently, CBZ2 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 4 and the maximum quantum efficiency is 6.0%.

Figure 5:
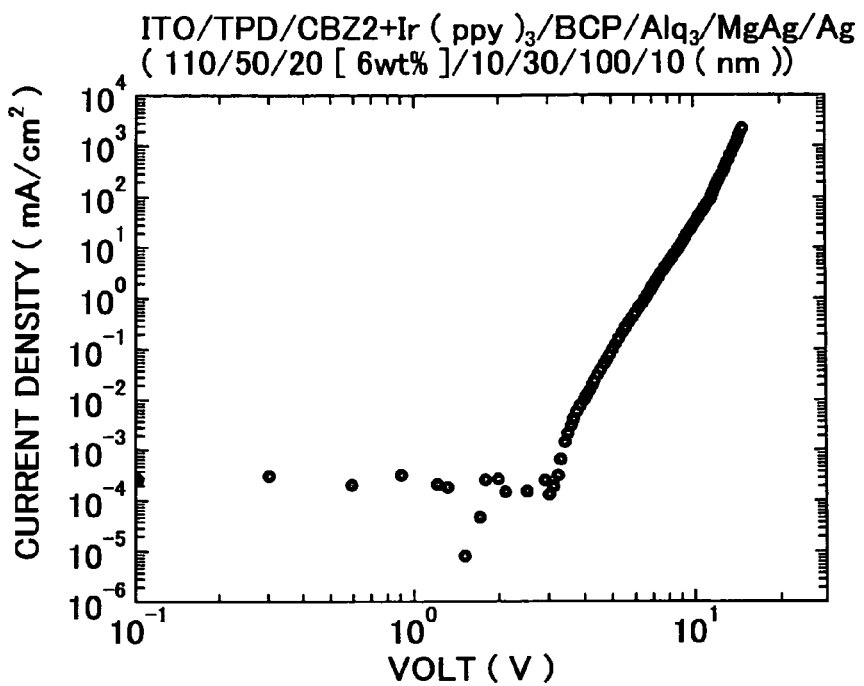
FIG. 5 is a graph showing the relationship between the current and the voltage of the organic electroluminescent device of Example 2.
Figure 6:
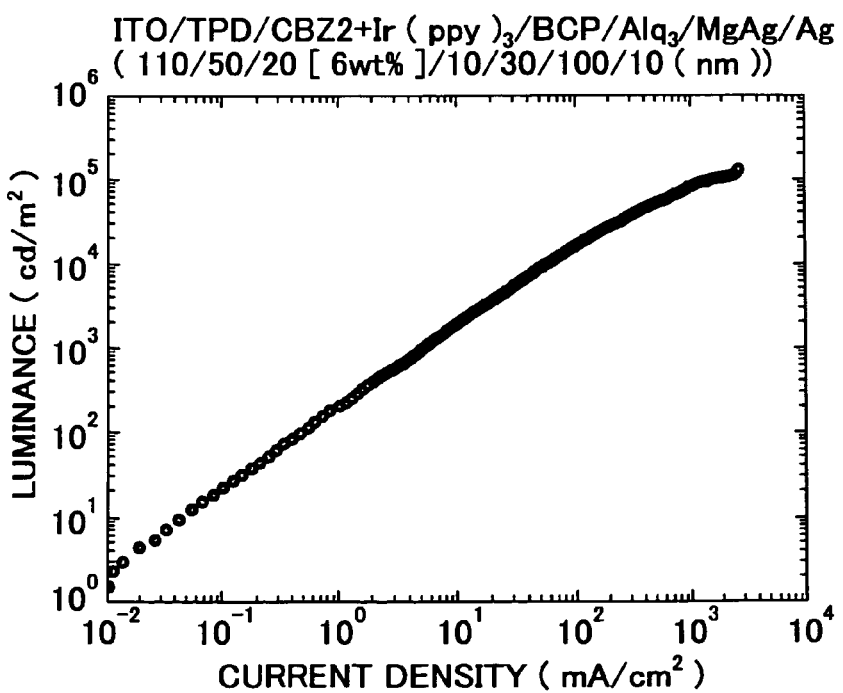
FIG. 6 is a graph showing the relationship between the current and the luminance of the organic electroluminescent device of Example 2.

In addition, the device has an excellent current-voltage characteristic as shown in FIG. 5. Specifically, the maximum current density is 2.575 A/cm$^2$ and the maximum luminance is 131,078 cd/m$^2$ (FIG. 6) when the applied voltage is 14.9 V. In addition, light having an emission spectrum such that a peak is observed at 512 nm was emitted from Ir(ppy)$_3$.

EXAMPLE 3

Figure 7:
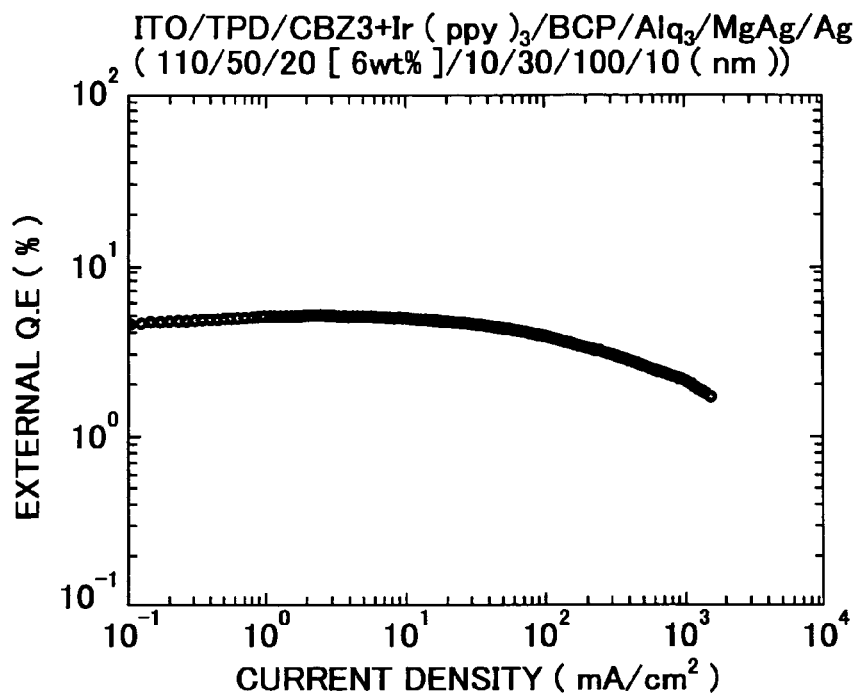
FIG. 7 is a graph showing the relationship between the current and the quantum efficiency of the organic electroluminescent device of Example 3.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of $10^{u-4}$ Pa to form a hole transporting layer with a thickness of 50 nm on the substrate. Subsequently, CBZ3 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 7 and the maximum quantum efficiency is 5.1%.

Figure 8:
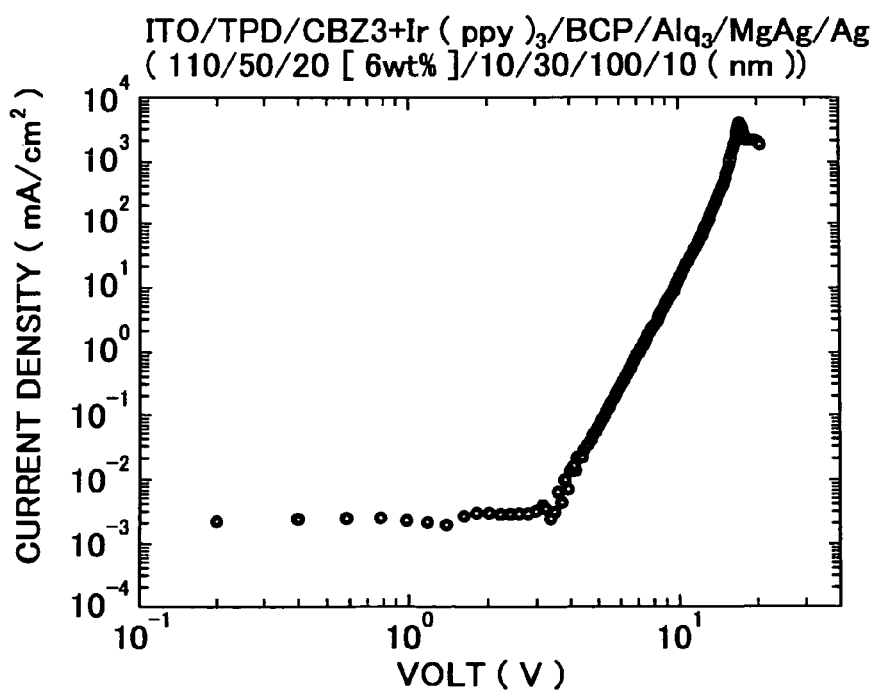
FIG. 8 is a graph showing the relationship between the current and the voltage of the organic electroluminescent device of Example 3.
Figure 9:
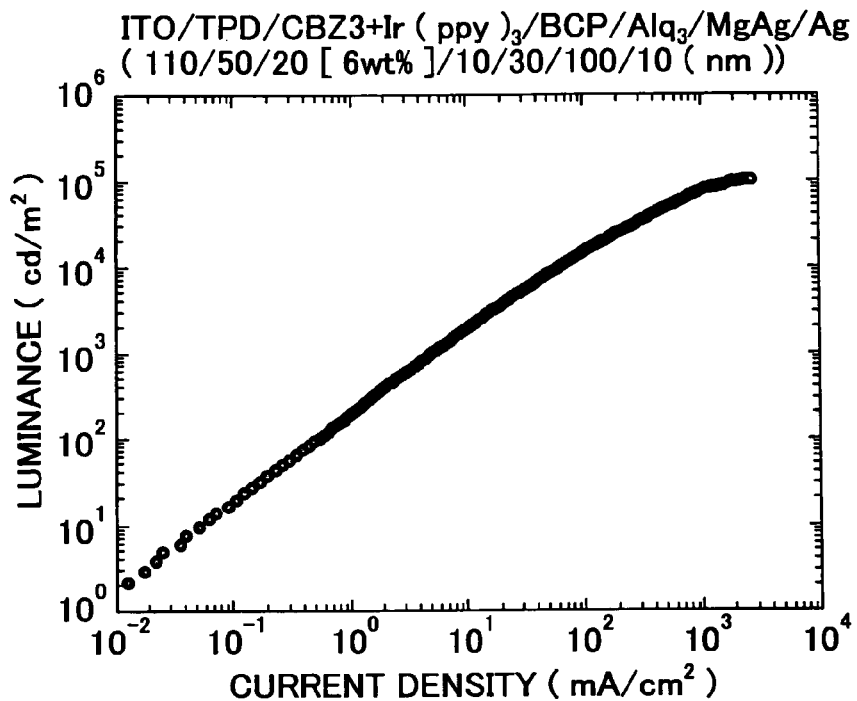
FIG. 9 is a graph showing the relationship between the current and the luminance of the organic electroluminescent device of Example 3.

In addition, the device has an excellent current-voltage characteristic as shown in FIG. 8. Specifically, the maximum current density is 2.670 A/cm$^2$ and the maximum luminance is 117,793 cd/m$^2$ (FIG. 9) when the applied voltage is 16.9 V. In addition, light having an emission spectrum such that a peak is observed at 512 nm was emitted from Ir(ppy)$_3$.

EXAMPLE 4

Figure 10:
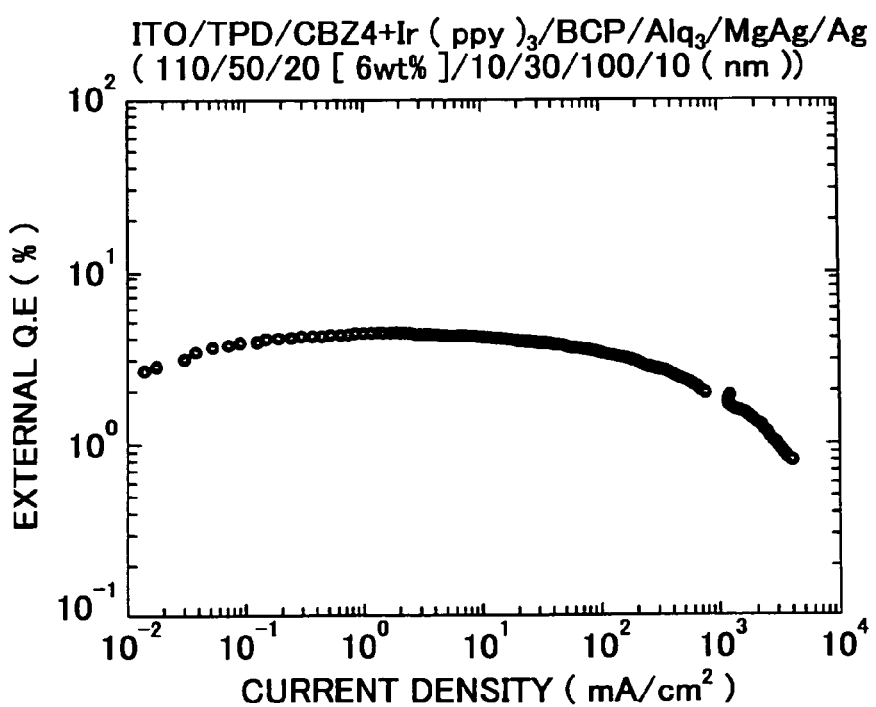
FIG. 10 is a graph showing the relationship between the current and the quantum efficiency of the organic electroluminescent device of Example 4.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ4 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 10 and the maximum quantum efficiency is 4.5%.

Figure 11:
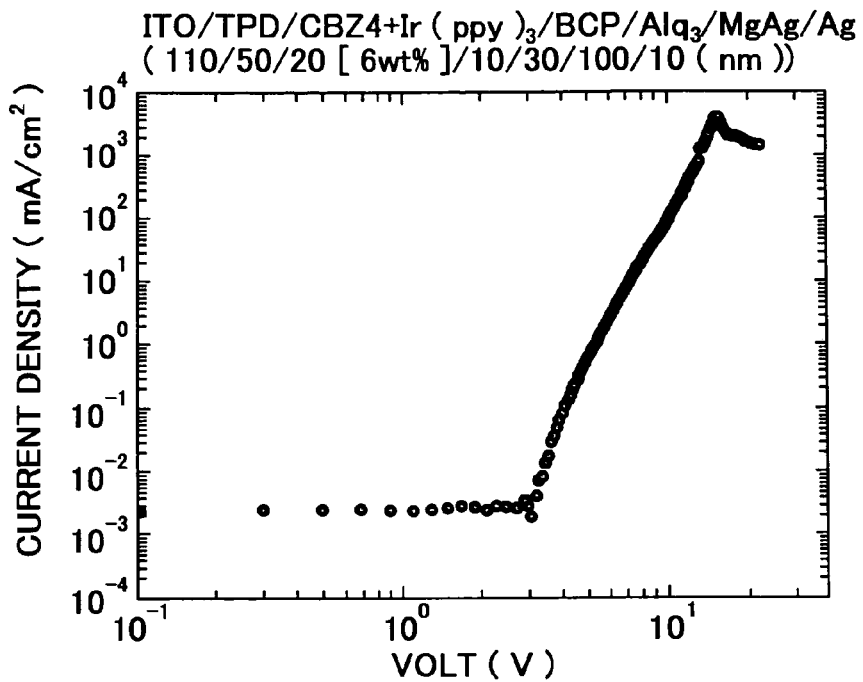
FIG. 11 is a graph showing the relationship between the current and the voltage of the organic electroluminescent device of Example 4.
Figure 12:
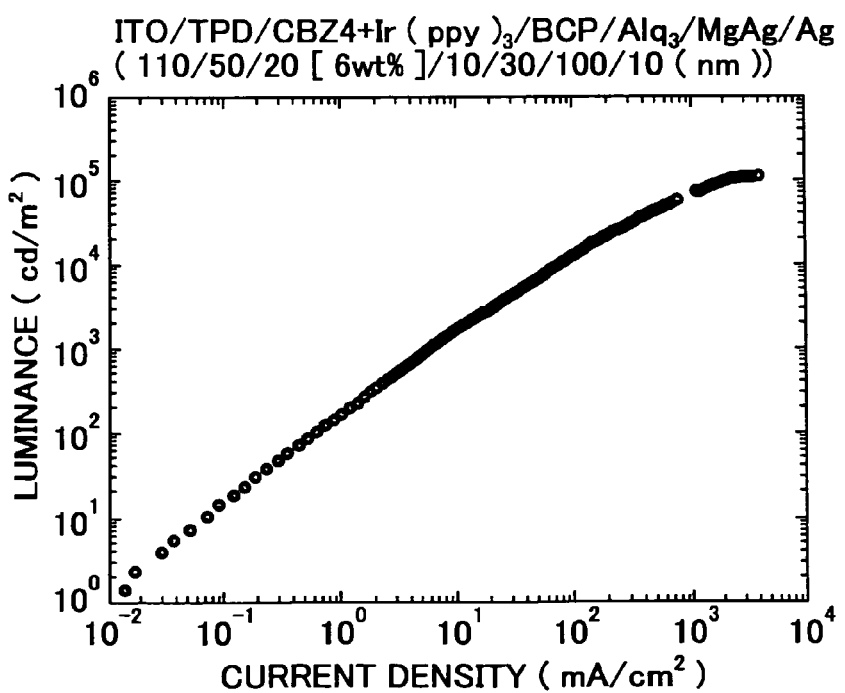
FIG. 12 is a graph showing the relationship between the current and the luminance of the organic electroluminescent device of Example 4.

In addition, the device has an excellent current-voltage characteristic as shown in FIG. 11. Specifically, the maximum current density is 3.715 A/cm$^2$ and the maximum luminance is 114,104 cd/m$^2$ (FIG. 12) when the applied voltage is 15.2. V. In addition, light having an emission spectrum such that a peak is observed at 510 nm was emitted from Ir(ppy)$_3$.

EXAMPLE 5

Figure 13:
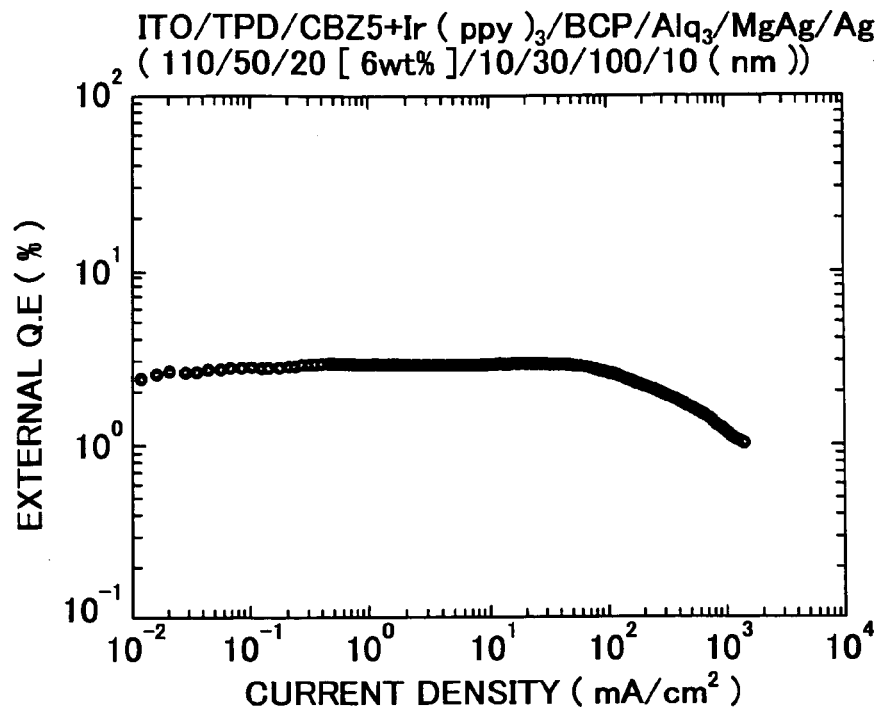
FIG. 13 is a graph showing the relationship between the current and the quantum efficiency of the organic electroluminescent device of Example 5.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was. deposited in a vacuum of 10$^{-4}$ Pa to form a hole transporting layer with a thickness of 50 nm on the substrate. Subsequently, CBZ5 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 13 and the maximum quantum efficiency is 3.1%.

Figure 14:
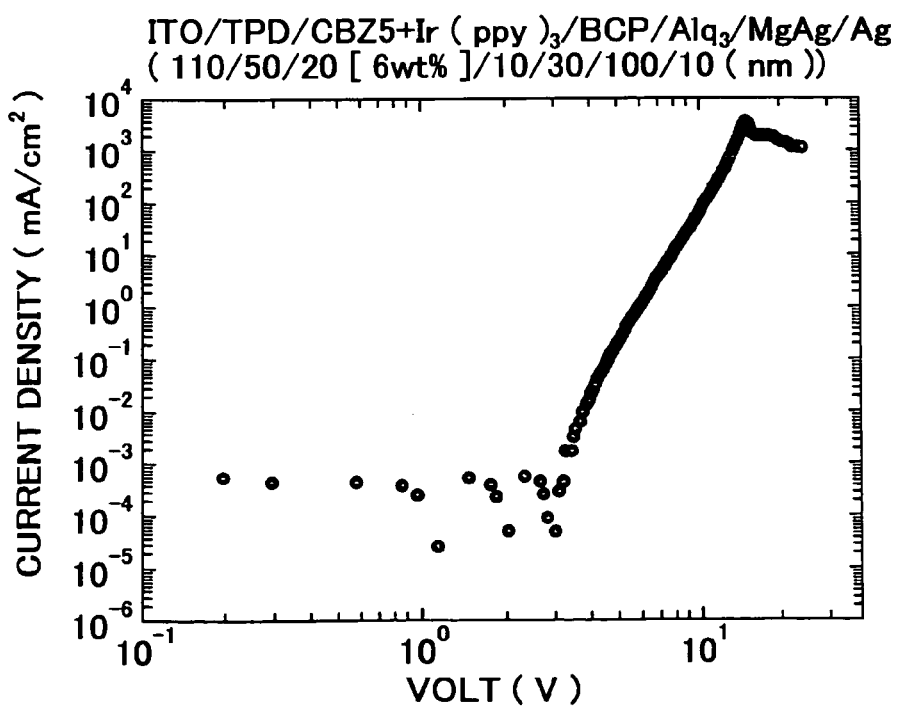
FIG. 14 is a graph showing the relationship between the current and the voltage of the organic electroluminescent device of Example 5.
Figure 15:
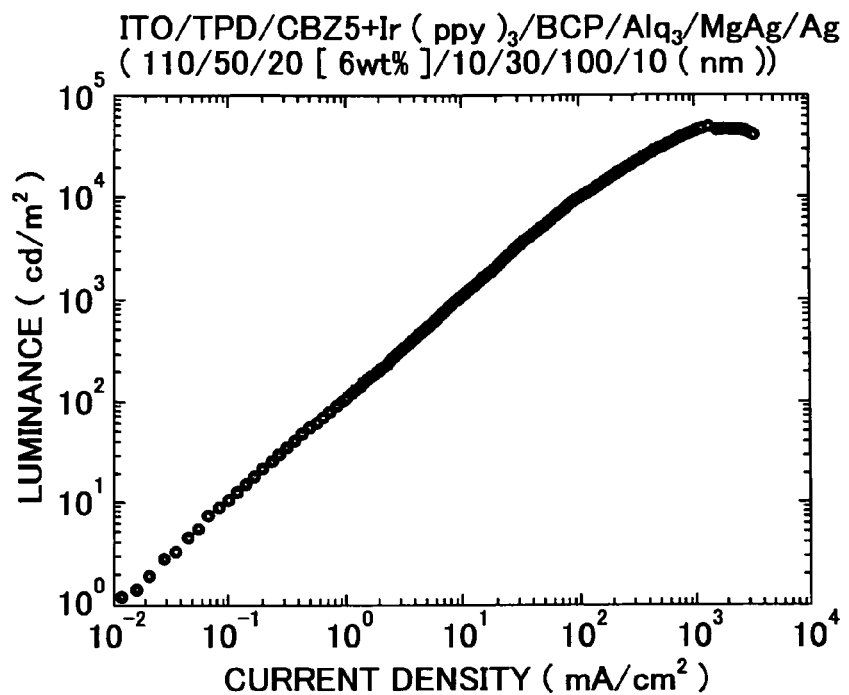
FIG. 15 is a graph showing the relationship between the current and the luminance of the organic electroluminescent device of Example 5.

In addition, the device has an excellent current-voltage characteristic as shown in FIG. 14. Specifically, the maximum current density is 1.408 A/cm$^2$ and the maximum luminance is 48,747 cd/m$^2$ (FIG. 15) when the applied voltage is 14.3 V. In addition, light having an emission spectrum such that a peak is observed at 509 nm was emitted from Ir(ppy)$_3$.

EXAMPLE 6

Figure 16:
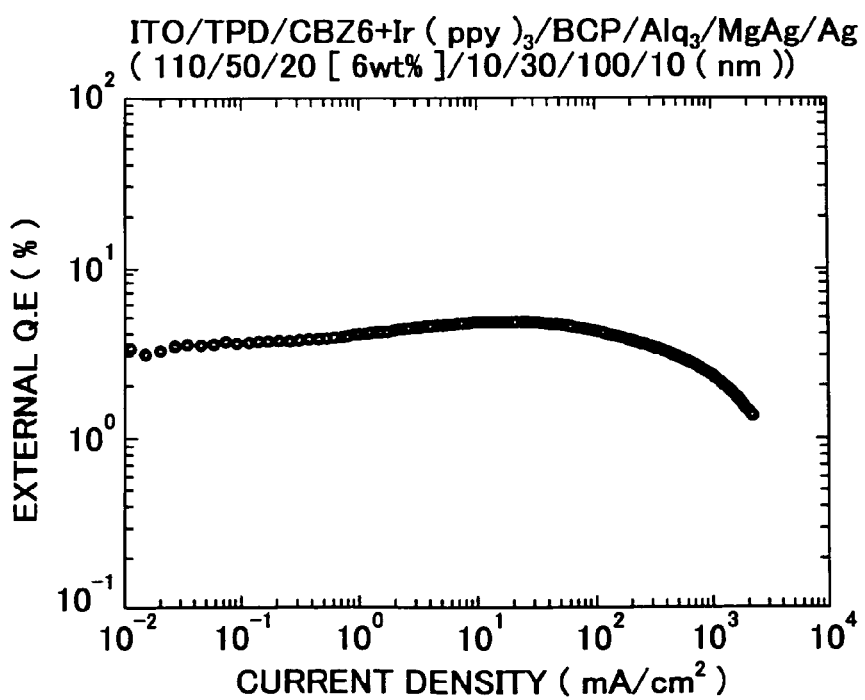
FIG. 16 is a graph showing the relationship between the current and the quantum efficiency of the organic electroluminescent device of Example 6.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ6 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 16 and the maximum quantum efficiency is 4.8%.

Figure 17:
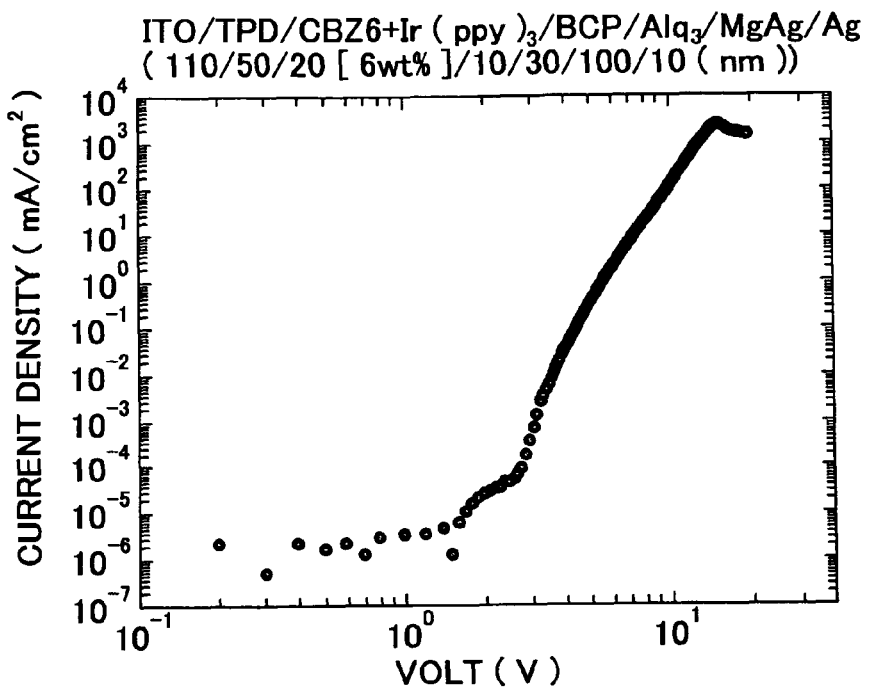
FIG. 17 is a graph showing the relationship between the current and the voltage of the organic electroluminescent device of Example 6.
Figure 18:
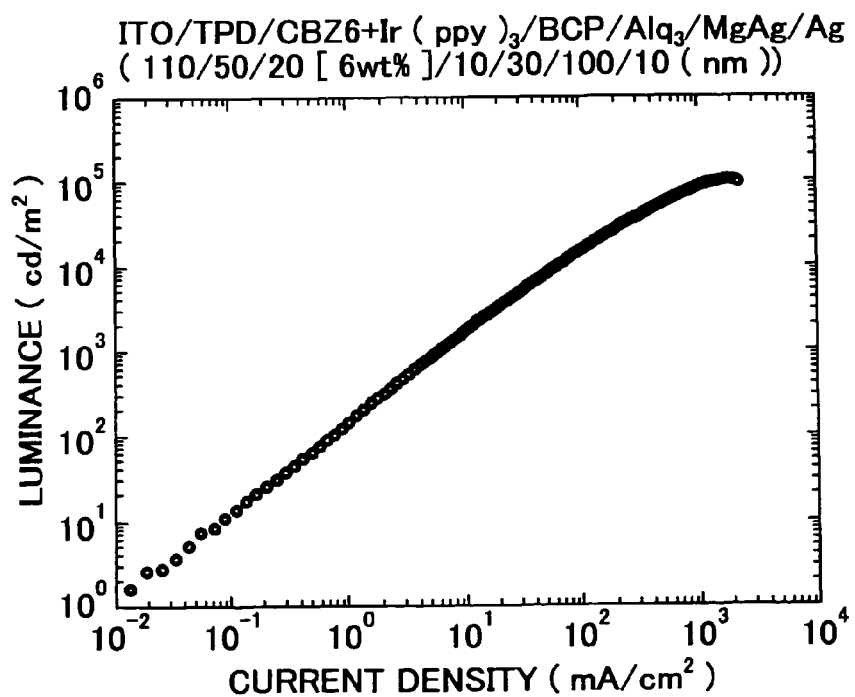
FIG. 18 is a graph showing the relationship between the current and the luminance of the organic electroluminescent device of Example 6.

In addition, the device has an excellent current-voltage characteristic as shown in FIG. 17. Specifically, the maximum current density is 2.115 A/cm$^2$ and the maximum luminance is 101,601 cd/m$^2$ (FIG. 18) when the applied voltage is 15.2 V. In addition, light having an emission spectrum such that a peak is observed at 508 nm was emitted from Ir(ppy)$_3$.

EXAMPLE 7

Figure 19:
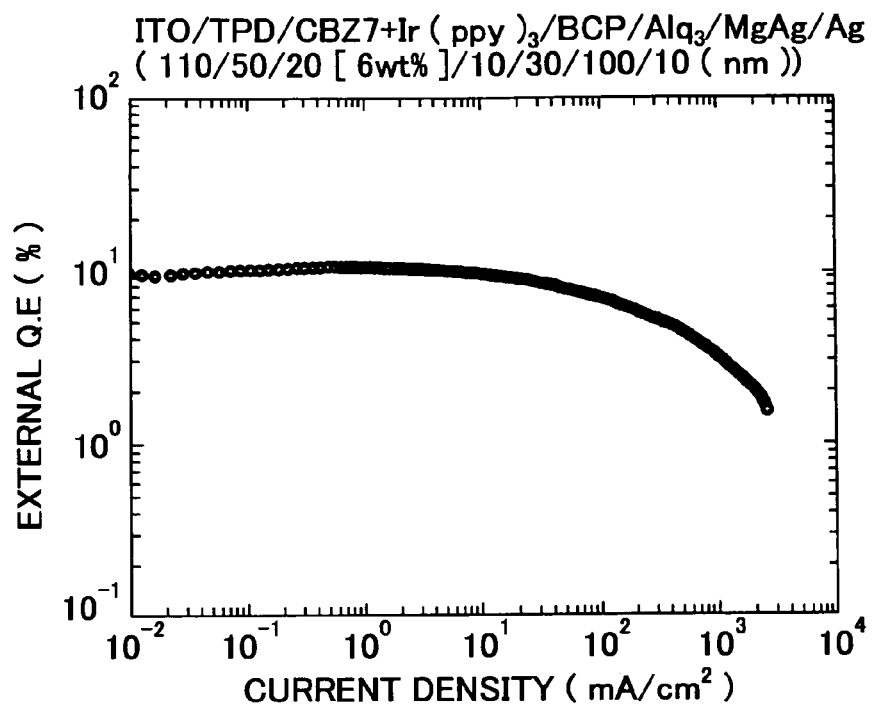
FIG. 19 is a graph showing the relationship between the current and the quantum efficiency of the organic electroluminescent device of Example 7.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ7 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 19 and the maximum quantum efficiency is 11.2%.

Figure 20:
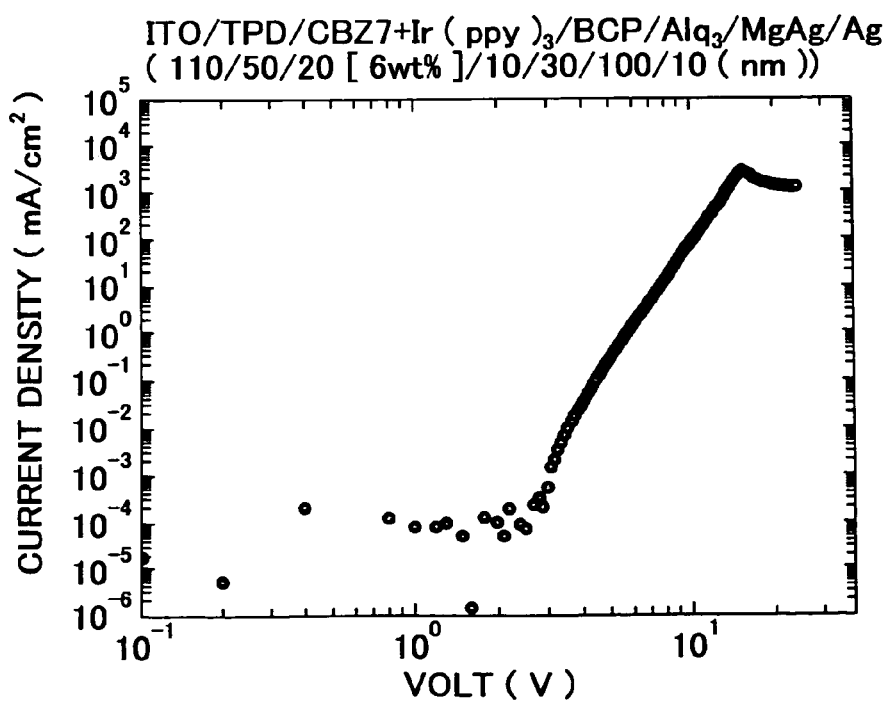
FIG. 20 is a graph showing the relationship between the current and the voltage of the organic electroluminescent device of Example 7.
Figure 21:
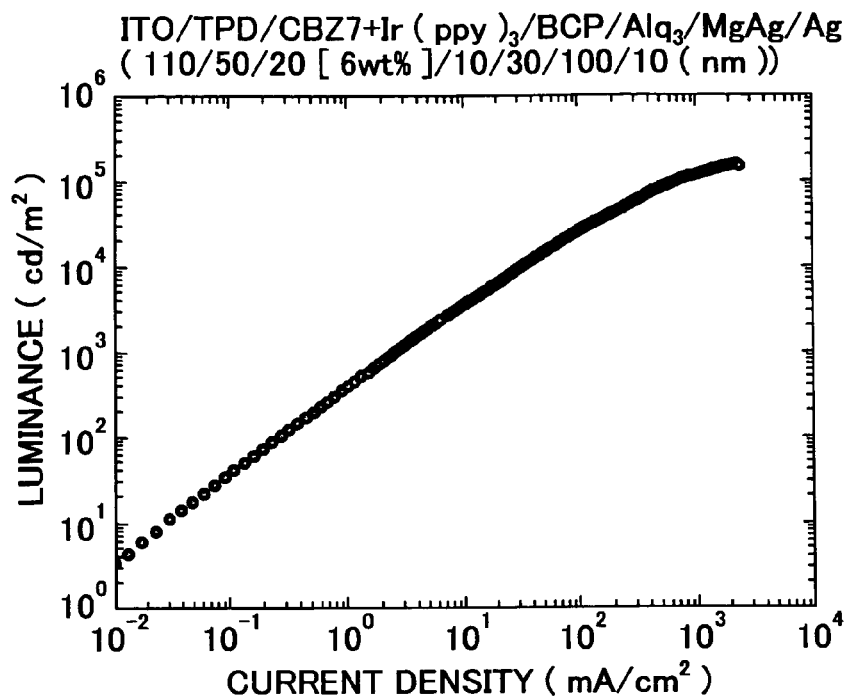
FIG. 21 is a graph showing the relationship between the current and the luminance of the organic electroluminescent device of Example 7.

In addition, the device has an excellent current-voltage characteristic as shown in FIG. 20. Specifically, the maximum current density is 2.640 A/cm$^2$ and the maximum luminance is 132,412 cd/m$^2$ (FIG. 21) when the applied voltage is 15.8 V. In addition, light having an emission spectrum such that a peak is observed at 511 nm was emitted from Ir(ppy)$_3$.

EXAMPLE 8

Figure 22:
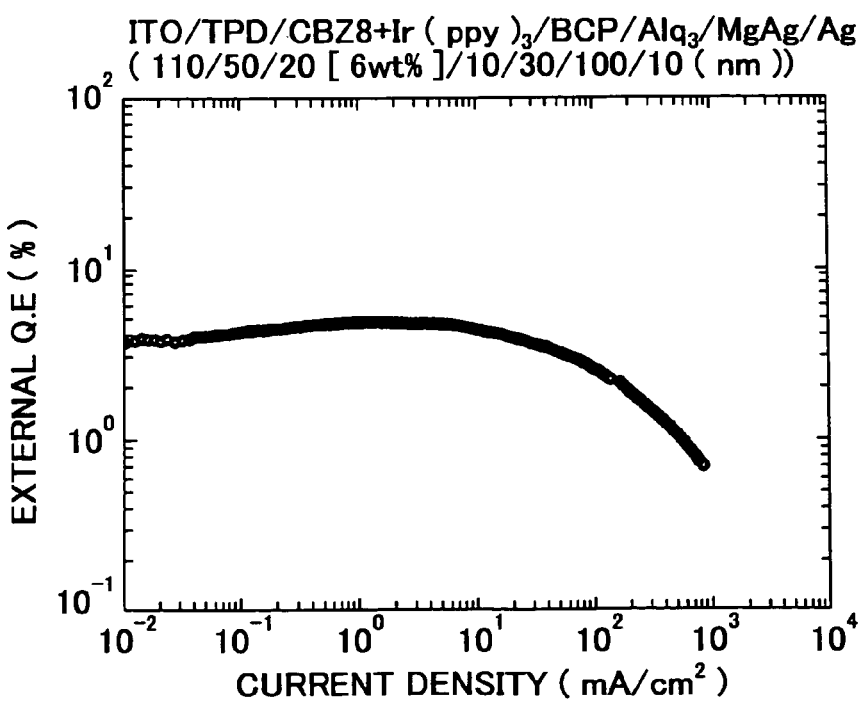
FIG. 22 is a graph showing the relationship between the current and the quantum efficiency of the organic electroluminescent device of Example 8.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$Pa to form a hole transporting layer with a thickness of 50 nm on the substrate. Subsequently, CBZ8 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 22 and the maximum quantum efficiency is 5.0%.

Figure 23:
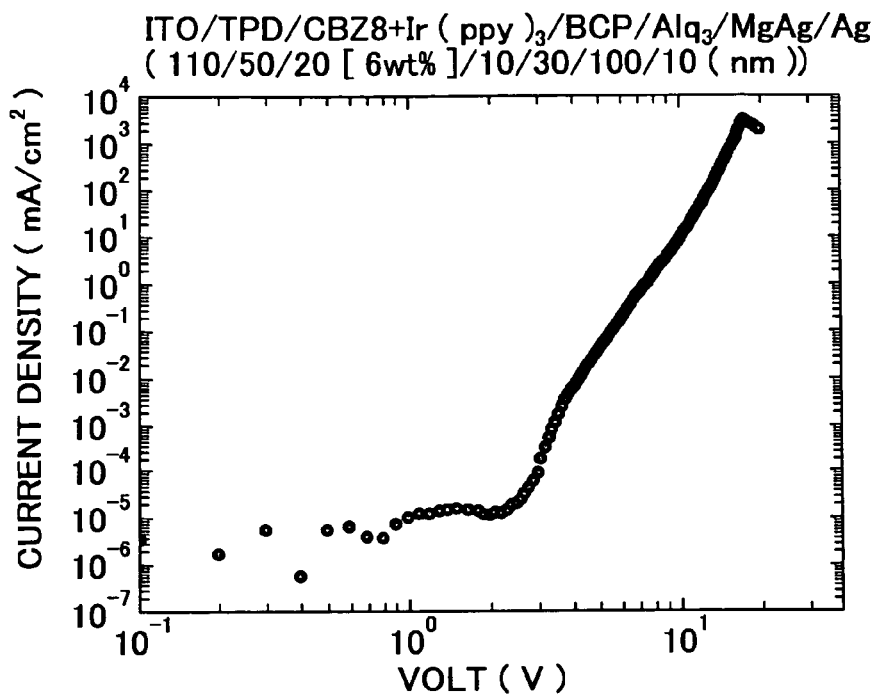
FIG. 23 is a graph showing the relationship between the current and the voltage of the organic electroluminescent device of Example 8.
Figure 24:
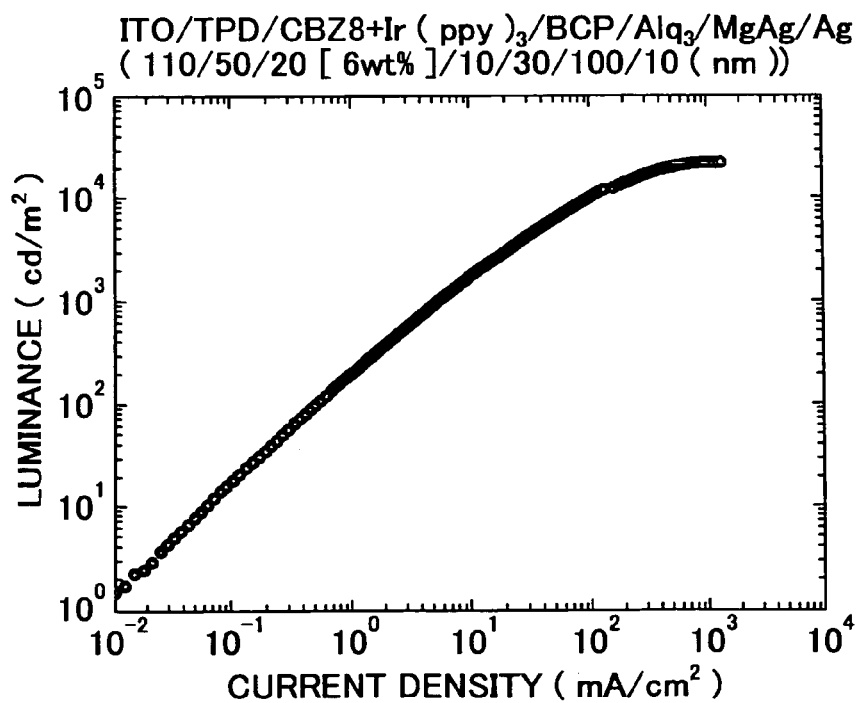
FIG. 24 is a graph showing the relationship between the current and the luminance of the organic electroluminescent device of Example 8.

In addition, the device has an excellent current-voltage characteristic as shown in FIG. 23. Specifically, the maximum current density is 1.012 A/cm$^2$ and the maximum luminance is 22,035 cd/m$^2$ (FIG. 24) when the applied voltage is 16.1 V. In addition, light having an emission spectrum such that a peak is observed at 508 nm was emitted from Ir(ppy)$_3$.

EXAMPLE 9

Figure 25:
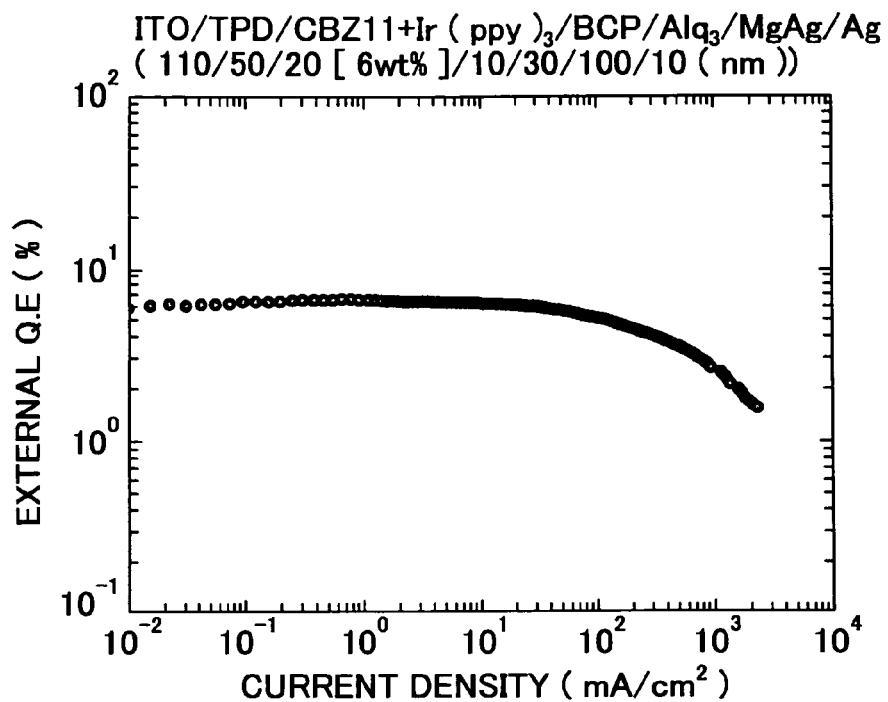
FIG. 25 is a graph showing the relationship between the current and the quantum efficiency of the organic electroluminescent device of Example 9.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ11 and Ir(ppy)$_3$ were co-deposited to form a luminescent layer with a thickness of 20 nm on the hole transporting layer. At this time, the concentration of Ir(ppy)$_3$ was kept at 6 percent by-weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 25 and the maximum quantum efficiency is 6.7%.

Figure 26:
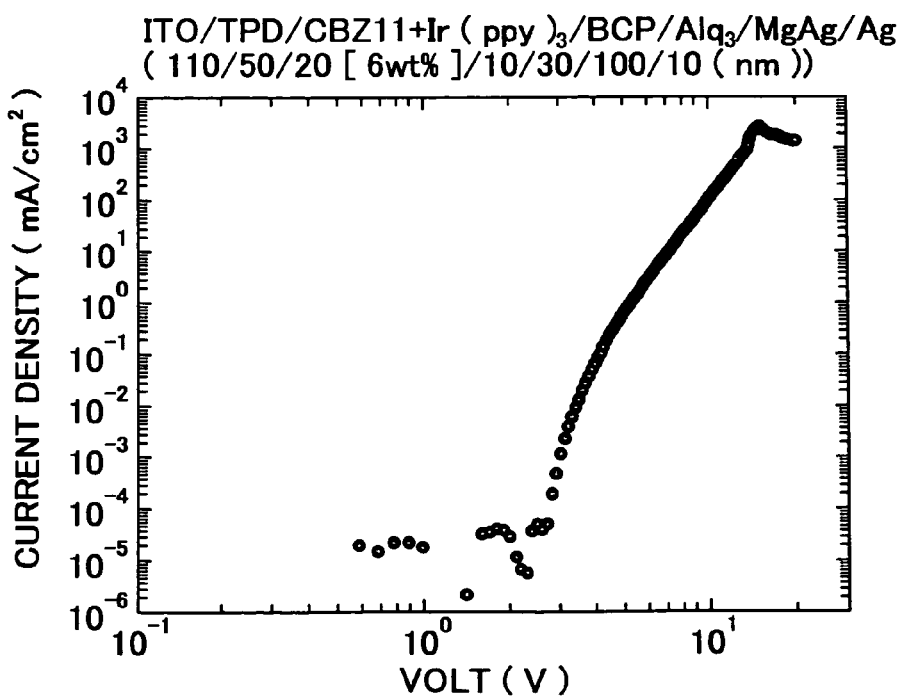
FIG. 26 is a graph showing the relationship between the current and the voltage of the organic electroluminescent device of Example 9.
Figure 27:
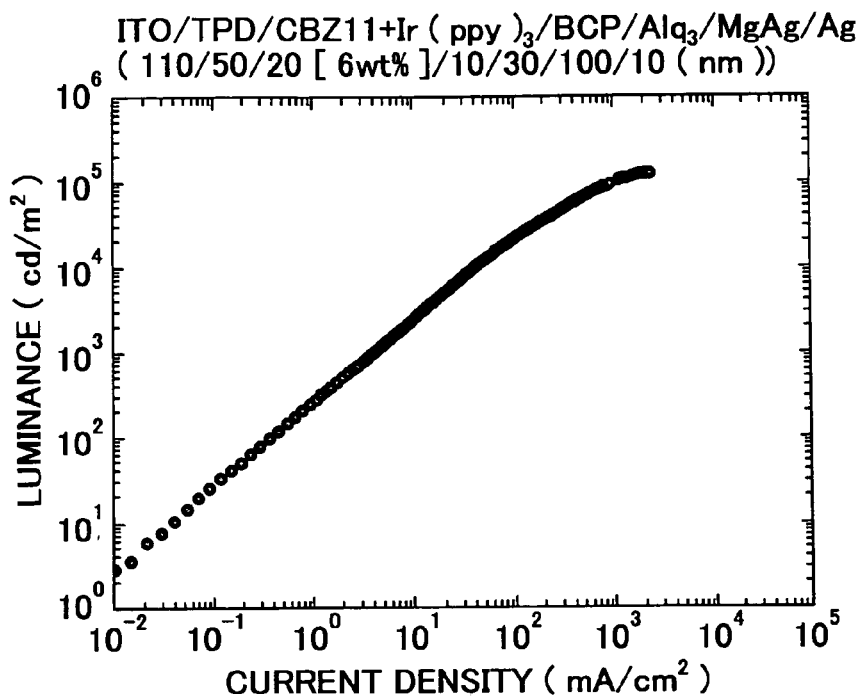
FIG. 27 is a graph showing the relationship between the current and the luminance of the organic electroluminescent device of Example 9.

In addition, the device has an excellent current-voltage characteristic as shown in FIG. 26. Specifically, the maximum current density is 2.386 A/cm$^2$ and the maximum luminance is 127,522 cd/m$^2$ (FIG. 27) when the applied voltage is 14.5 V. In addition, light having an emission spectrum such that a peak is observed at 512 nm was emitted from Ir(ppy)$_3$.

EXAMPLE 10

Figure 28:
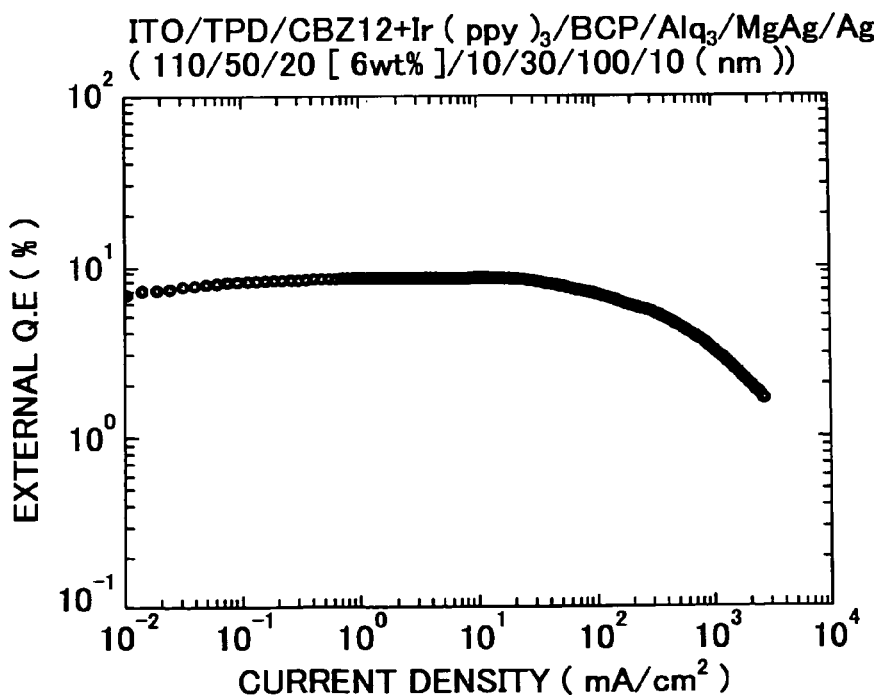
FIG. 28 is a graph showing the relationship between the current and the quantum efficiency of the organic electroluminescent device of Example 10.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ12 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 28 and the maximum quantum efficiency is 9.2%.

Figure 29:
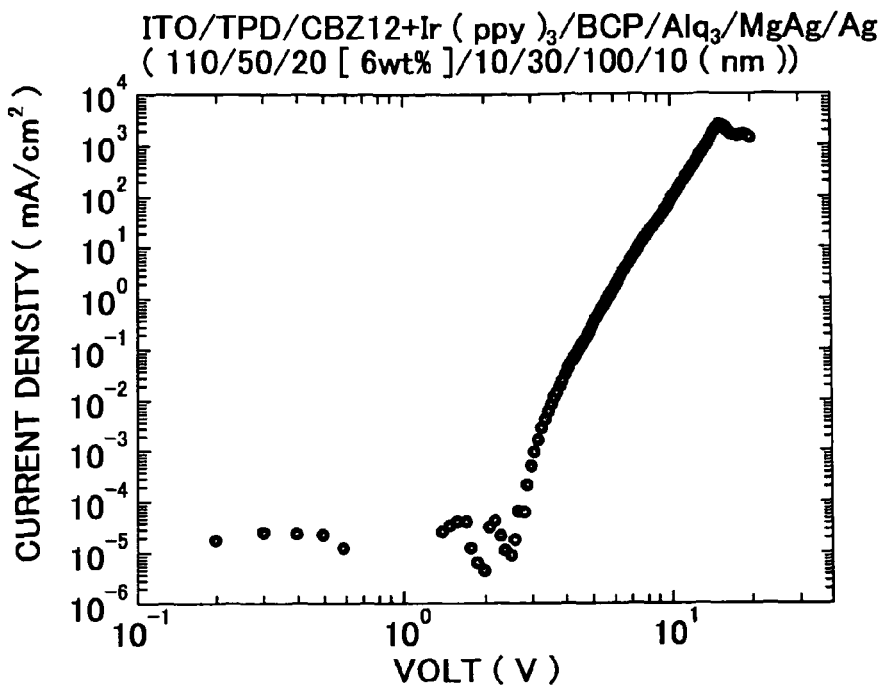
FIG. 29 is a graph showing the relationship between the current and the voltage of the organic electroluminescent device of Example 10.
Figure 30:
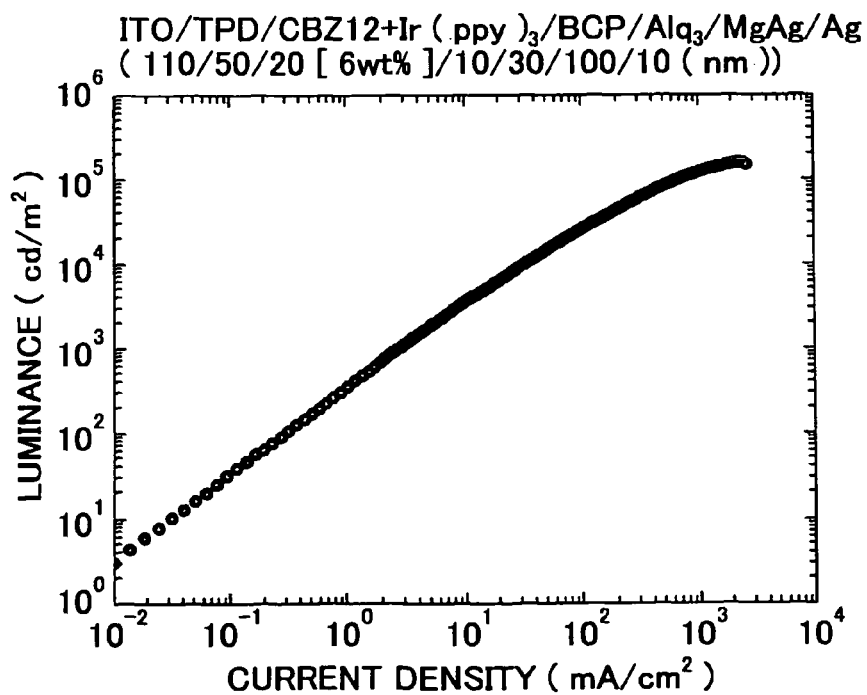
FIG. 30 is a graph showing the relationship between the current and the luminance of the organic electroluminescent device of Example 10.

In addition, the device has an excellent current-voltage characteristic as shown in FIG. 29. Specifically, the maximum current density is 2.605 A/cm$^2$ and the maximum luminance is 154,756 cd/m$^2$ (FIG. 30) when the applied voltage is 15.5 V. In addition, light having an emission spectrum such that a peak is observed at 509 nm was emitted from Ir(ppy)$_3$.

EXAMPLE 11

Figure 31:
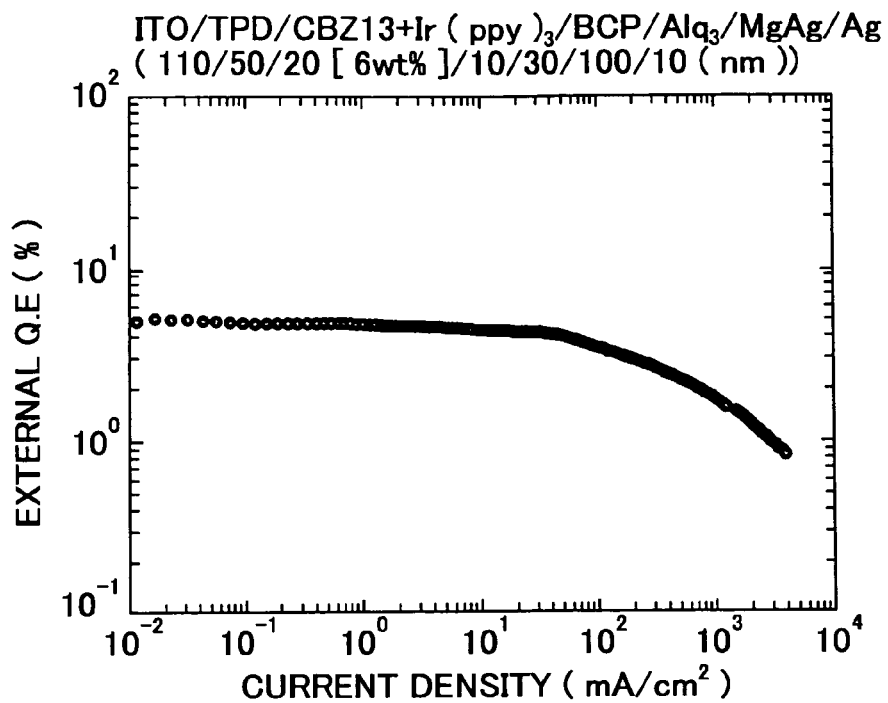
FIG. 31 is a graph showing the relationship between the current and the quantum efficiency of the organic electroluminescent device of Example 11.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ13 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 31 and the maximum quantum efficiency is 5.5%.

Figure 32:
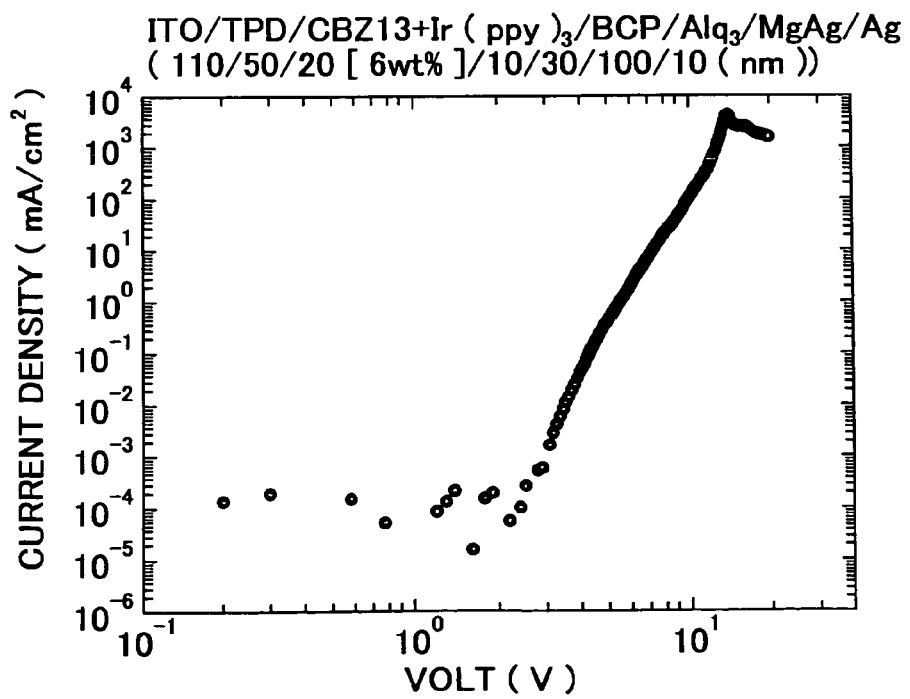
FIG. 32 is a graph showing the relationship between the current and the voltage of the organic electroluminescent device of Example 11.
Figure 33:
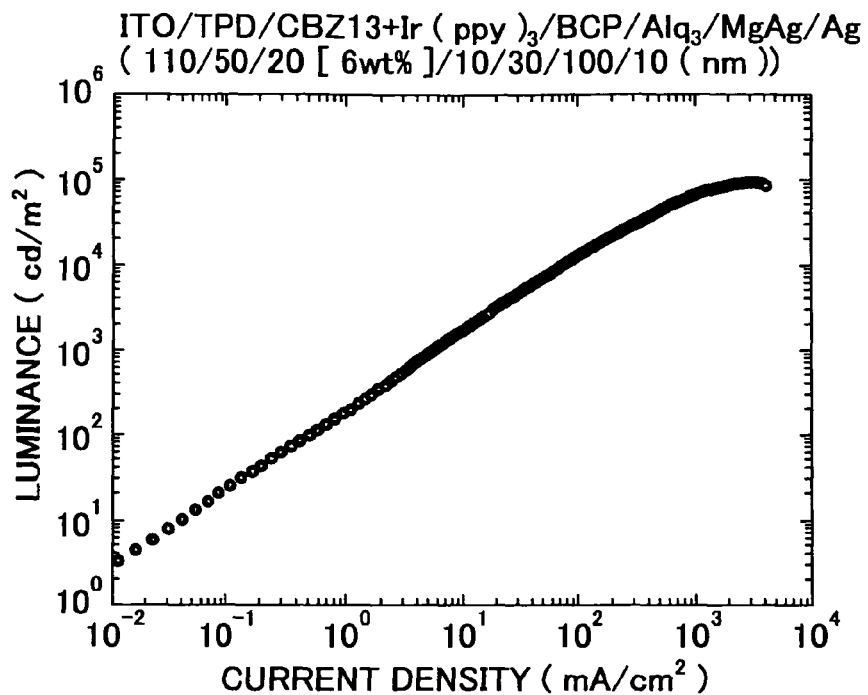
FIG. 33 is a graph showing the relationship between the current and the luminance of the organic electroluminescent device of Example 11.

In addition, the device has an excellent current-voltage characteristic as shown in FIG. 32. Specifically, the maximum current density is 4.269 A/cm2 and the maximum luminance is 91,595 cd/m$^2$ (FIG. 33) when the applied voltage is 14.2 V. In addition, light having an emission spectrum such that a peak is observed at 508 nm was emitted from Ir(ppy)$_3$.

EXAMPLE 12

Figure 34:
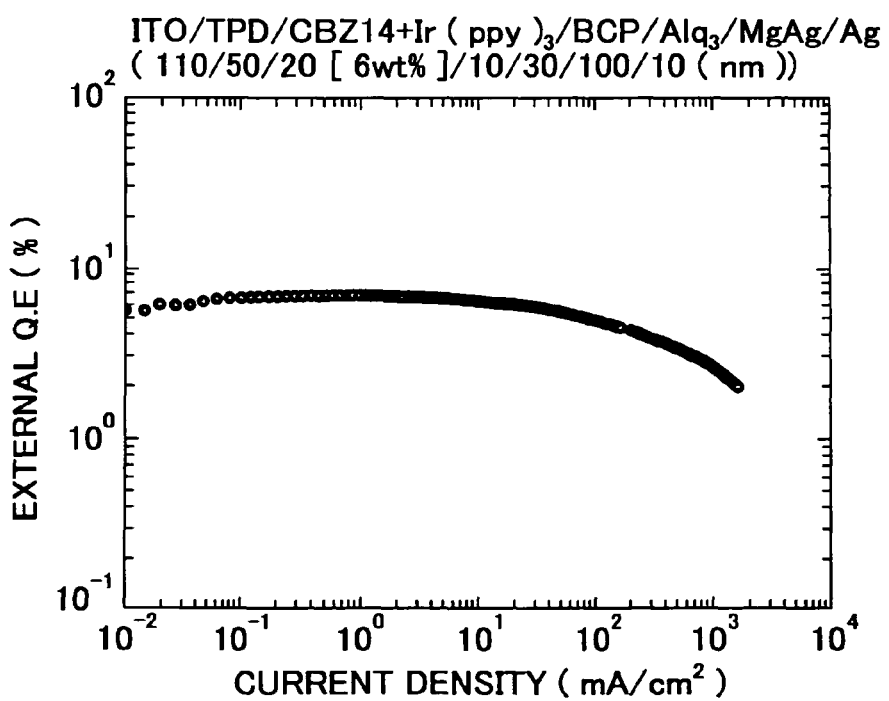
FIG. 34 is a graph showing the relationship between the current and the quantum efficiency of the organic electroluminescent device of Example 12.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ14 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 34 and the maximum quantum efficiency is 7.0%.

Figure 35:
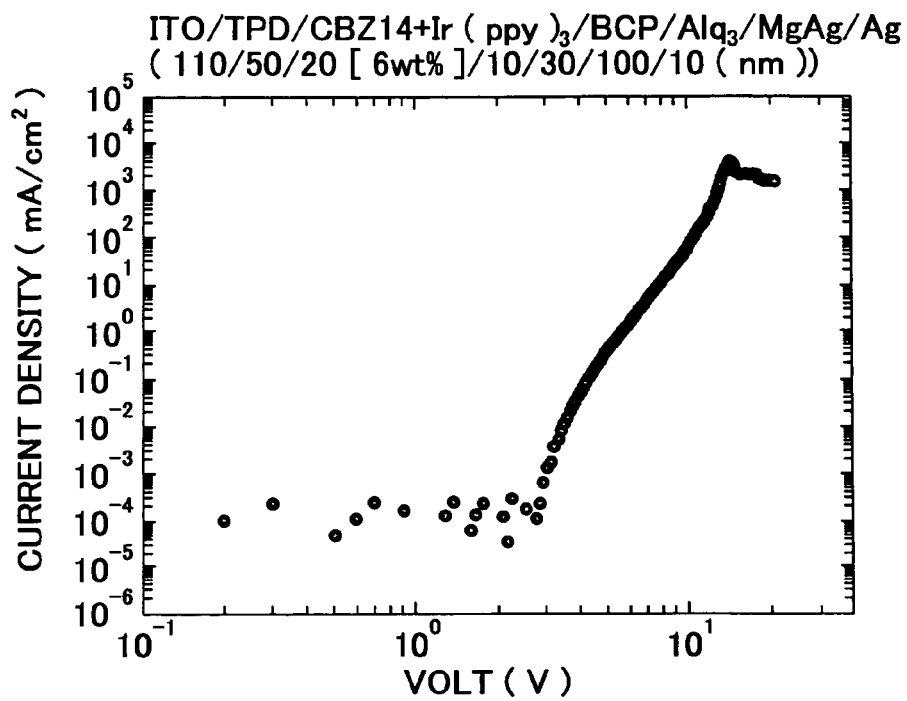
FIG. 35 is a graph showing the relationship between the current and the voltage of the organic electroluminescent device of Example 12.
Figure 36:
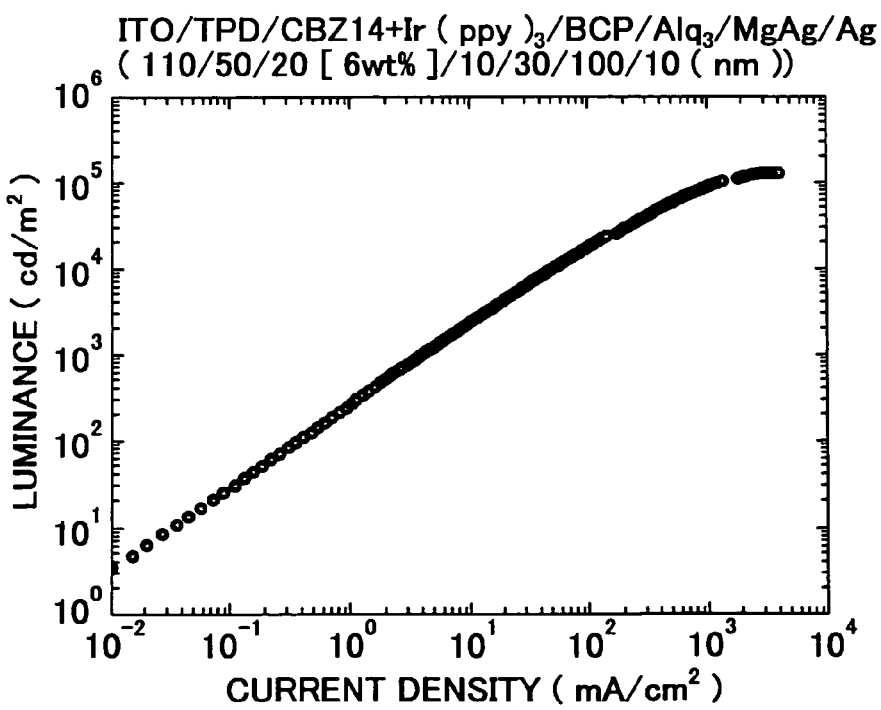
FIG. 36 is a graph showing the relationship between the current and the luminance of the organic electroluminescent device of Example 12.

In addition, the device has an excellent current-voltage characteristic as shown in FIG. 35. Specifically, the maximum current density is 4.317 A/cm$^2$ and the maximum luminance is 128,782 cd/m$^2$ (FIG. 36) when the applied voltage is 14.7 V. In addition, light having an emission spectrum such that a peak is observed at 512 nm was emitted from Ir(ppy)$_3$.

EXAMPLE 13

Figure 37:
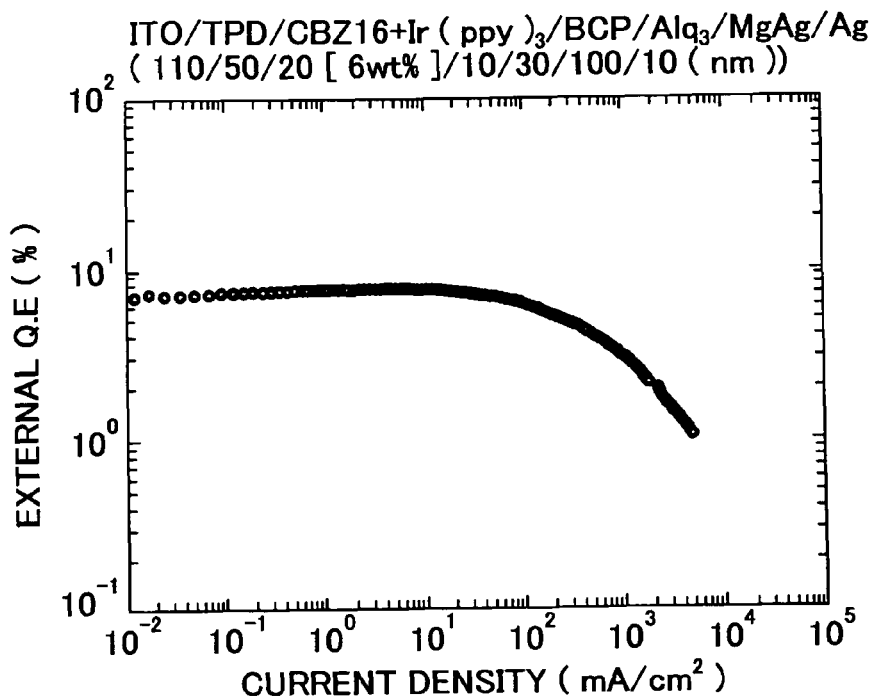
FIG. 37 is a graph showing the relationship between the current and the quantum efficiency of the organic electroluminescent device of Example 13.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ16 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 37 and the maximum quantum efficiency is 7.9%.

Figure 38:
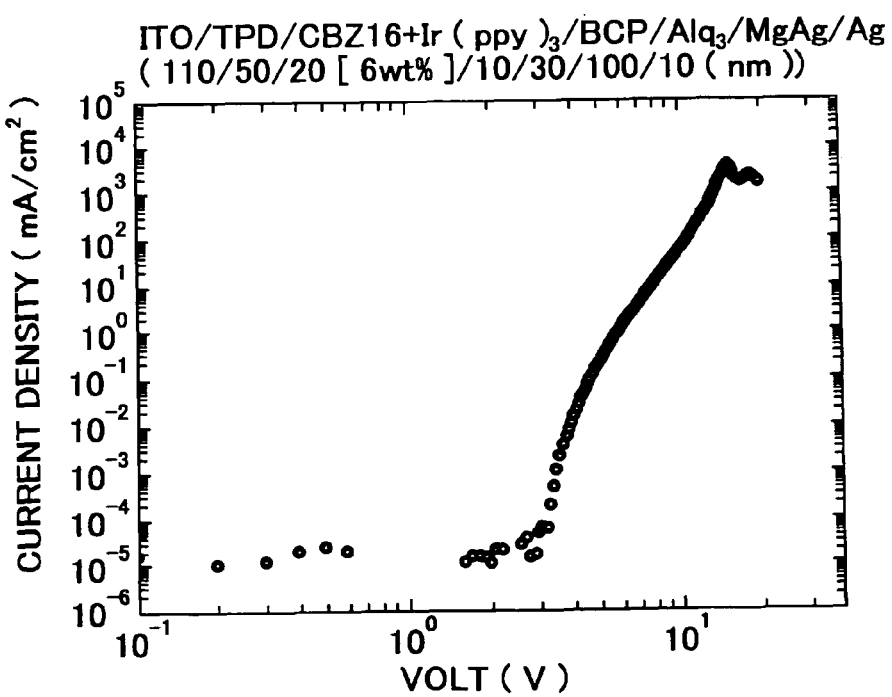
FIG. 38 is a graph showing the relationship between the current and the voltage of the organic electroluminescent device of Example 13.
Figure 39:
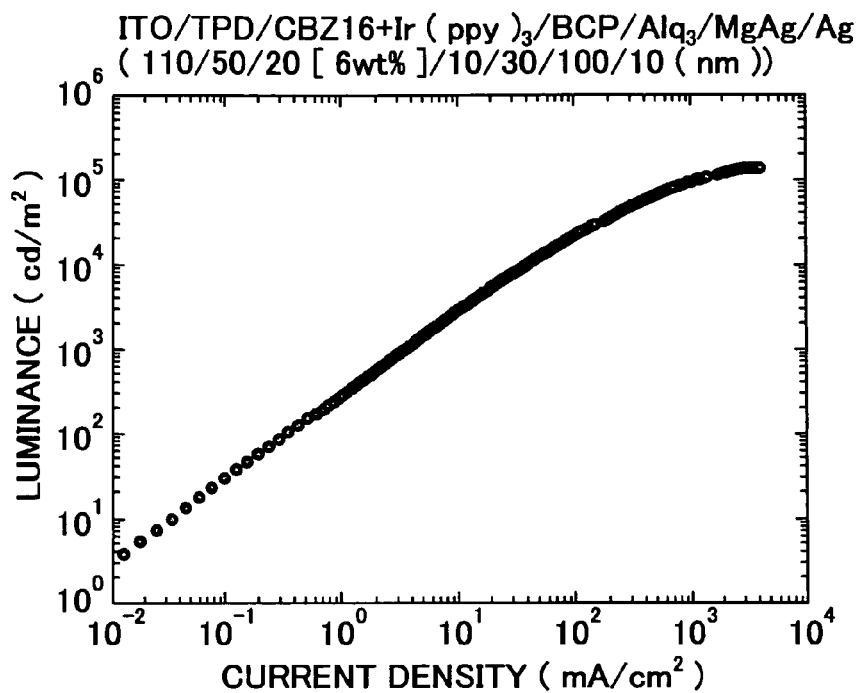
FIG. 39 is a graph showing the relationship between the current and the luminance of the organic electroluminescent device of Example 13.

In addition, the device has an excellent current-voltage characteristic as shown in FIG. 38. Specifically, the maximum current density is 3;737 A/cm$^2$ and the maximum luminance is 142,984 cd/m$^2$ (FIG. 39) when the applied voltage is 15.1 V. In addition, light having an emission spectrum such that a peak is observed at 512 nm was emitted from Ir(ppy)$_3$.

EXAMPLE 14

Figure 40:
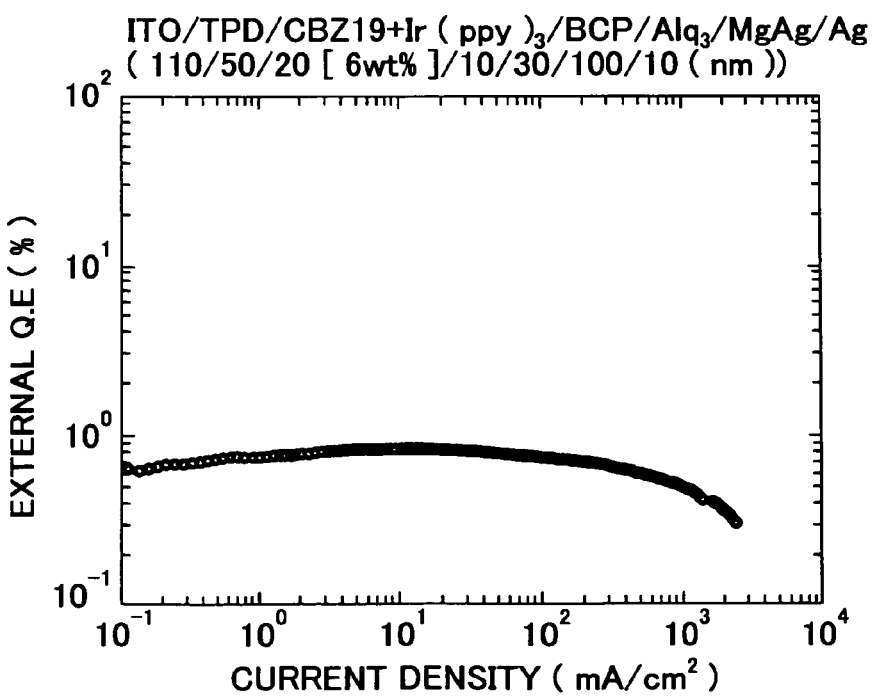
FIG. 40 is a graph showing the relationship between the current and the quantum efficiency of the organic electroluminescent device of Example 14.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ19 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 40 and the maximum quantum efficiency is 0.8%.

Figures 41, 42:
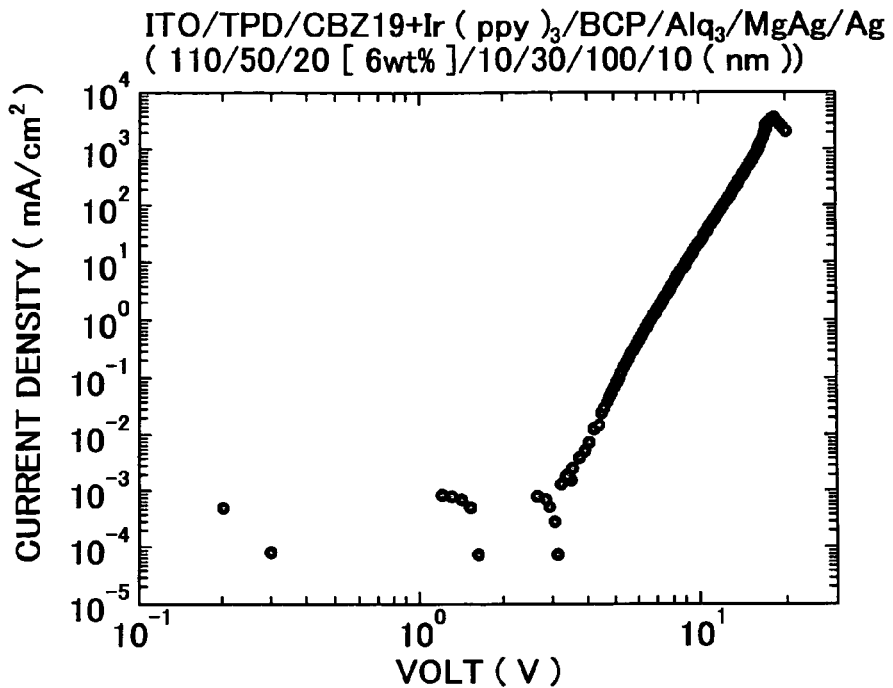
FIG. 41 is a graph showing the relationship between the -current and the voltage of the organic electroluminescent device of Example 14.
FIG. 42 is a graph showing the relationship between the current and the luminance of the organic electroluminescent device of Example 14.

In addition, the device has an excellent current-voltage characteristic as shown in FIG. 41. Specifically, the maximum current density is 2.594 A/cm$^2$ and the maximum luminance is 18,231 cd/m$^2$ (FIG. 42) when the applied voltage is 17.3 V. In addition, light having an emission spectrum such that a peak is observed at 510 nm was emitted from Ir(ppy)$_3$.

EXAMPLE 15

Figure 43:
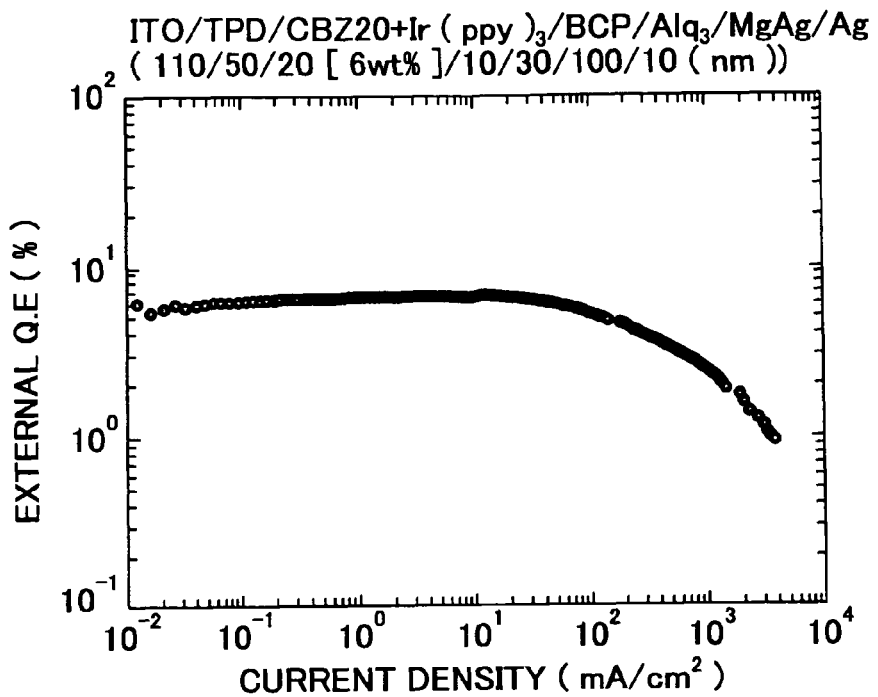
FIG. 43 is a graph showing the relationship between the current and the quantum efficiency of the organic electroluminescent device of Example 15.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ20 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 43 and the maximum quantum efficiency is 7.2%.

Figure 44:
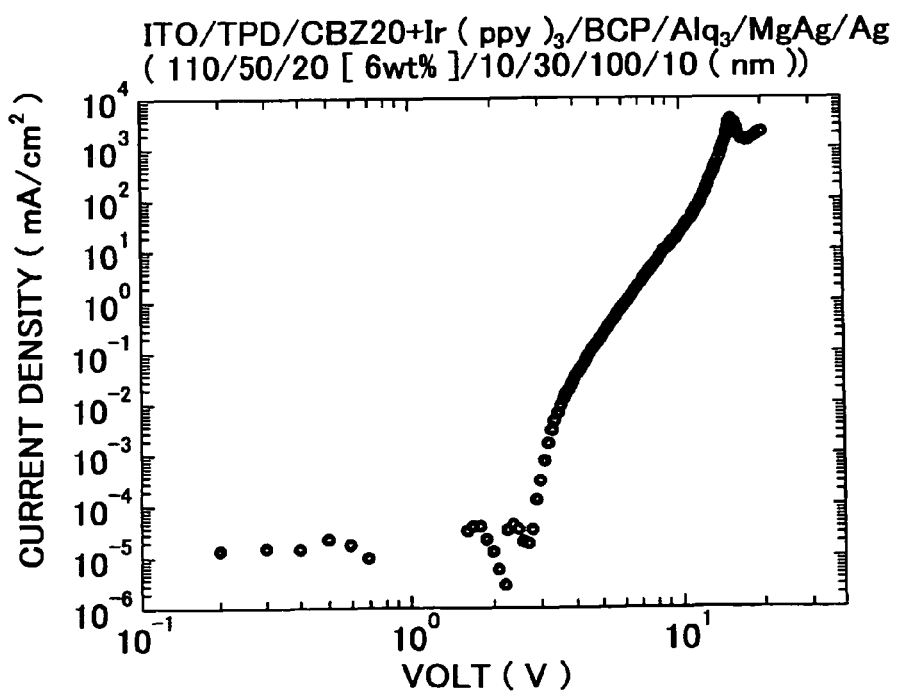
FIG. 44 is a graph showing the relationship between the current and the voltage of the organic electroluminescent device of Example 15.
Figure 45:
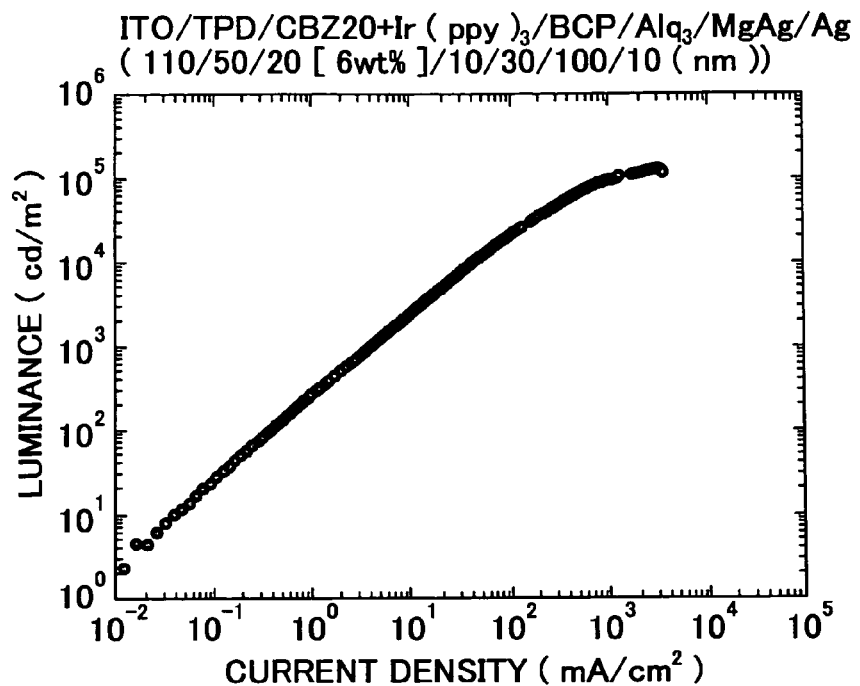
FIG. 45 is a graph showing the relationship between the current and the luminance of the organic electroluminescent device of Example 15.

In addition, the device has an excellent current-voltage characteristic as shown in FIG. 44. Specifically, the maximum current density is 3.384 A/cm$^2$ and the maximum luminance is 130,163 cd/m$^2$ (FIG. 42) when the applied voltage is 15.4 V. In addition, light having an emission spectrum such that a peak is observed at 512 nm was emitted from Ir(ppy)$_3$.

EXAMPLE 16

Figure 46:
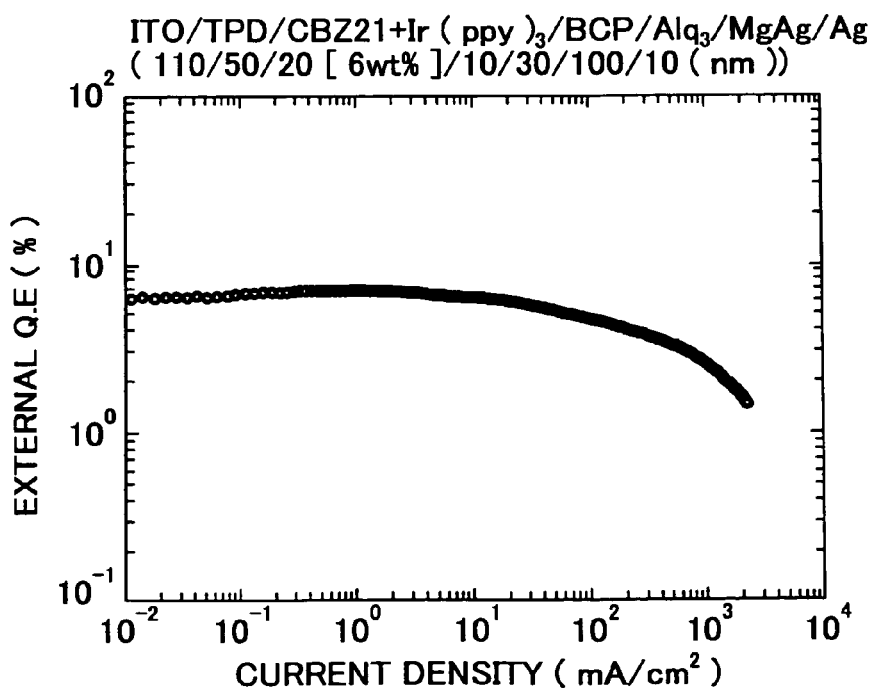
FIG. 46 is a graph showing the relationship between the current and the quantum efficiency of the organic electroluminescent device of Example 16.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ21 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 46 and the maximum quantum efficiency is 8.0%.

Figure 47:
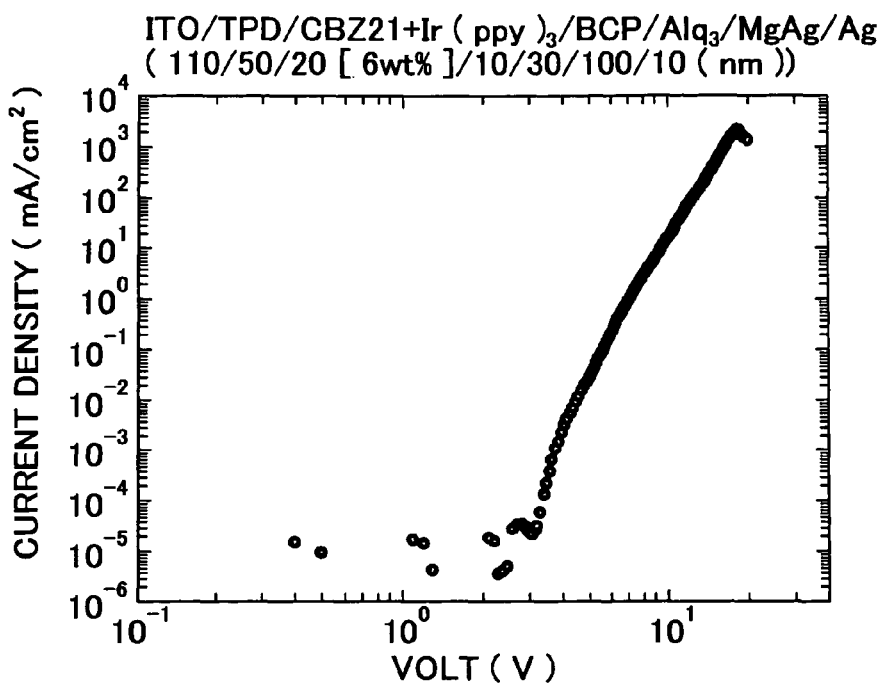
FIG. 47 is a graph showing the relationship between the current and the voltage of the organic electroluminescent device of Example 16.
Figure 48:
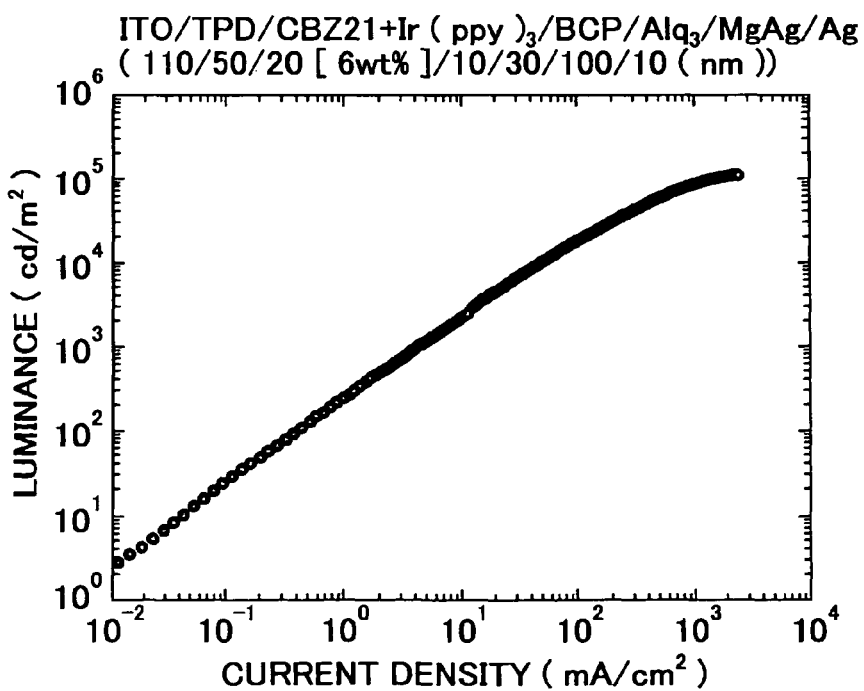
FIG. 48 is a graph showing the relationship between the current and the luminance of the organic electroluminescent device of Example 16.

In addition, the device has an excellent current-voltage voltage characteristic as shown in FIG. 47. Specifically, the maximum current density is 2.195 A/cm$^2$ and the maximum luminance is 119,564 cd/m$^2$ (FIG. 48) when the applied voltage is 18.0 V. In addition, light having an emission spectrum such that a peak is observed at 508 nm was emitted from Ir(ppy)$_3$.

EXAMPLE 17

Figure 49:
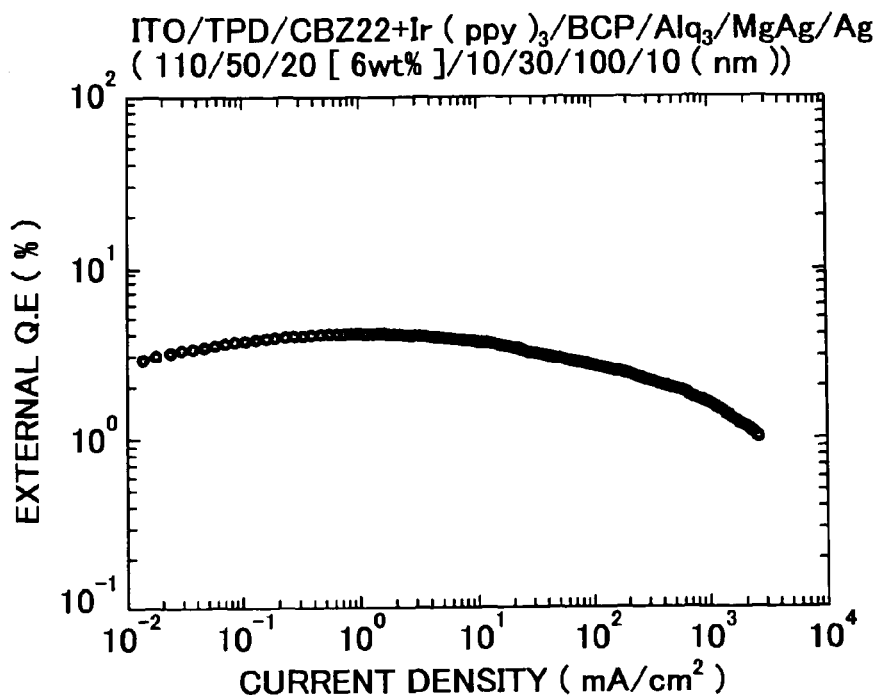
FIG. 49 is a graph showing the relationship between the current and the quantum efficiency of the organic electroluminescent device of Example 17.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of 10$^{-4}$ Pa to form a hole transporting layer with a thickness of 50 nm on the substrate. Subsequently, CBZ22 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 49 and the maximum quantum efficiency is 4.2%.

Figure 50:
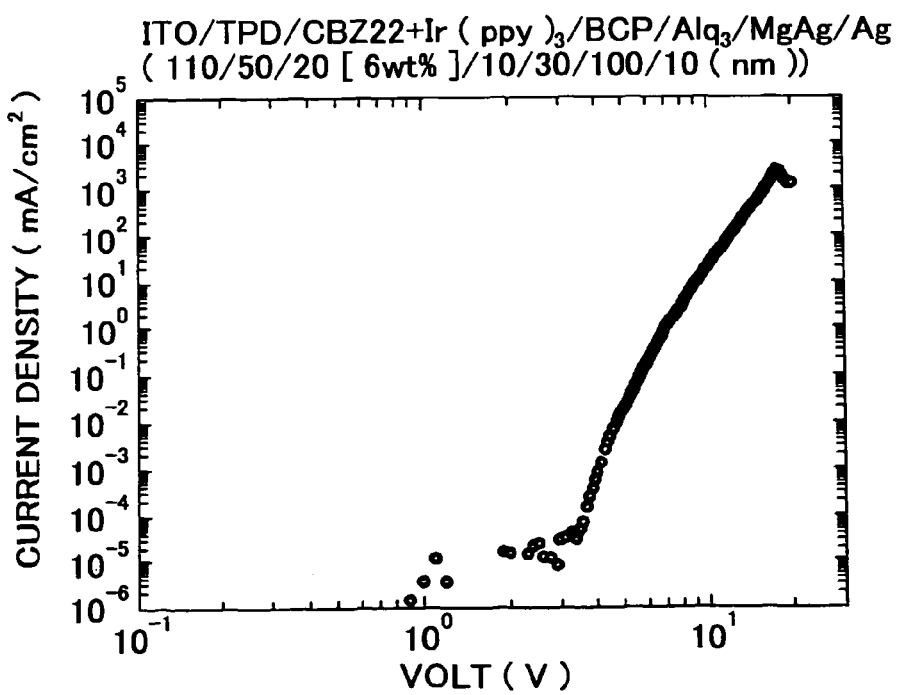
FIG. 50 is a graph showing the relationship between the current and the voltage of the organic electroluminescent device of Example 17.
Figure 51:
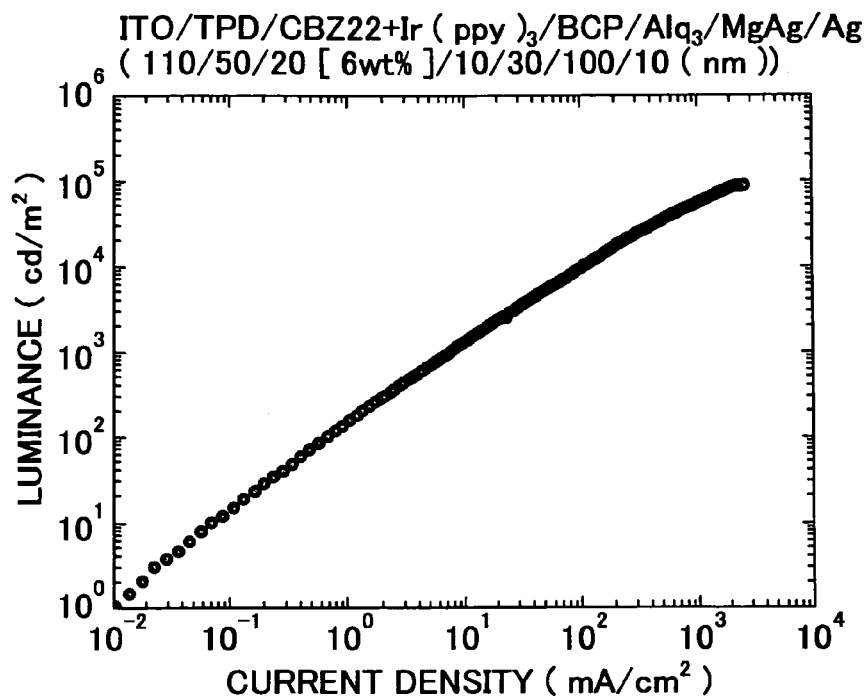
FIG. 51 is a graph showing the relationship between the current and the luminance of the organic electroluminescent device of Example 17.

In addition, the device has an excellent current-voltage characteristic as shown in FIG. 50. Specifically, the maximum current density is 2.698 A/cm$^2$ and the maximum luminance is 96,058 cd/m$^2$ (FIG. 51) when the applied voltage is 17.6 V. In addition, light having an emission spectrum such that a peak is observed at 508 nm was emitted from Ir(ppy)$_3$.

EXAMPLE 18

Figure 52:
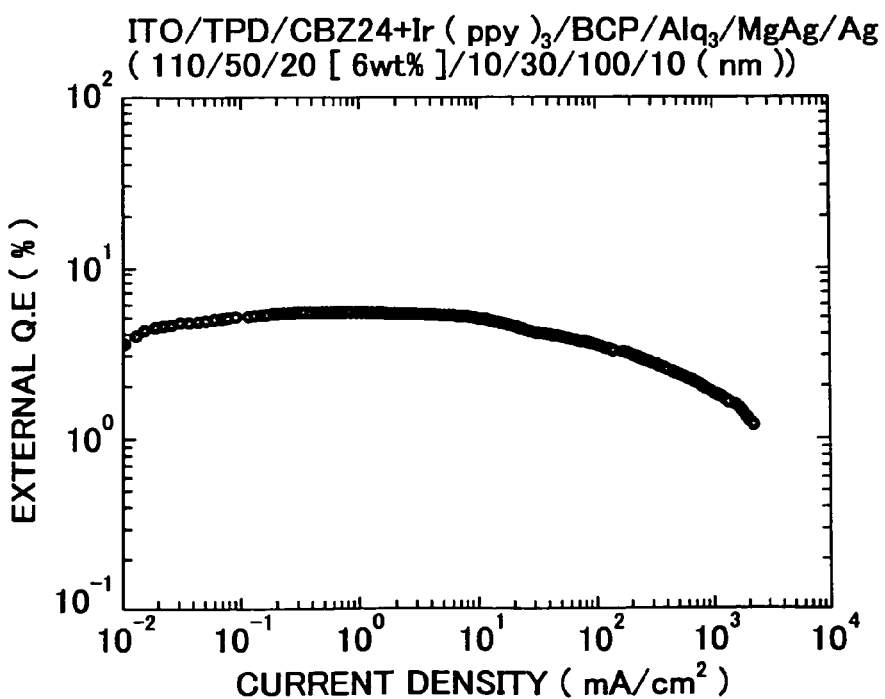
FIG. 52 is a graph showing the relationship between the current and the quantum efficiency of the organic electroluminescent device of Example 18.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of $10^{-4}$ Pa to form a hole transporting layer with a thickness of 50 nm on the substrate. Subsequently, CBZ24 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum-efficiency property of the device is shown in FIG. 52 and the maximum quantum efficiency is 5.5%.

Figure 53:
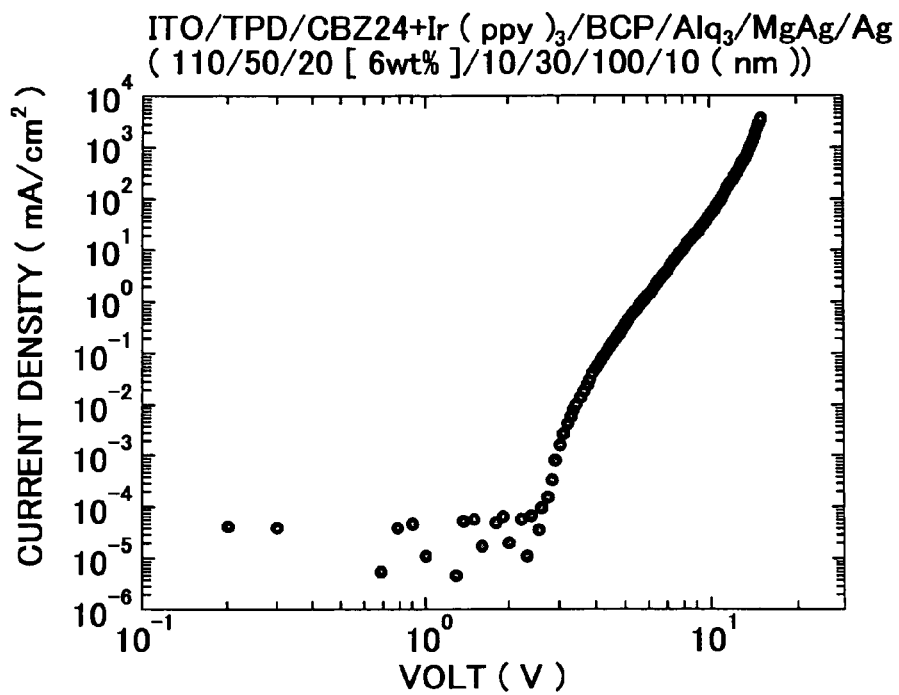
FIG. 53 is a graph showing the relationship between the current and the voltage of the organic electroluminescent device of Example 18.
Figure 54:
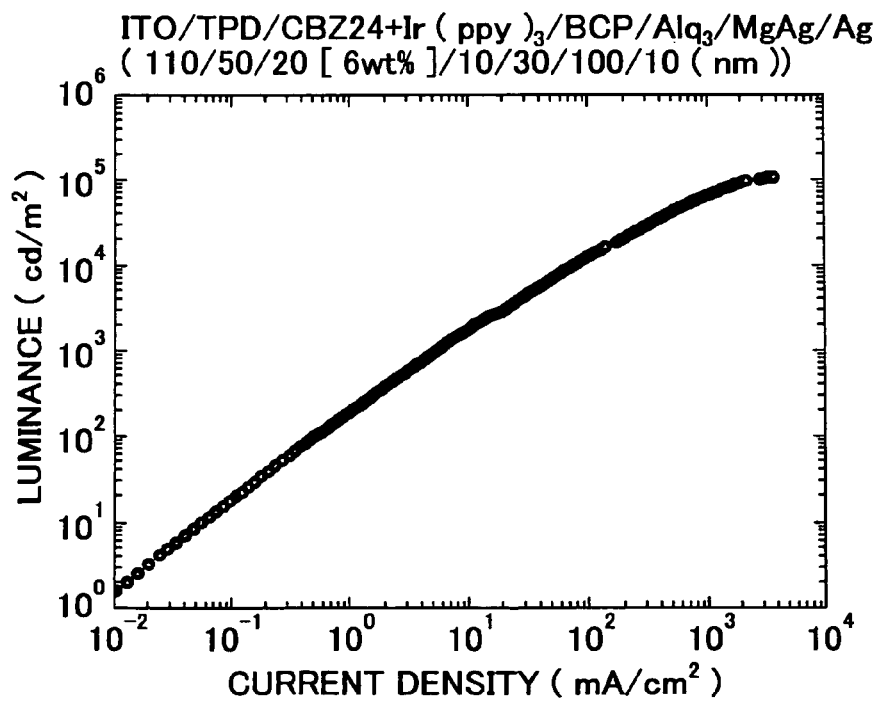
FIG. 54 is a graph showing the relationship between the current and the luminance of the organic electroluminescent device of Example 18.

In addition, the device has an excellent current-voltage characteristic as shown in FIG. 53. Specifically, the maximum current density is 3.565 A/cm$^2$ and the maximum luminance is 111,574 cd/m$^2$ (FIG. 54) when the applied voltage is 15.1 V. In addition, light having an emission spectrum such that a peak is observed at 512 nm was emitted from Ir(ppy)$_3$.

EXAMPLE 19

Figure 55:
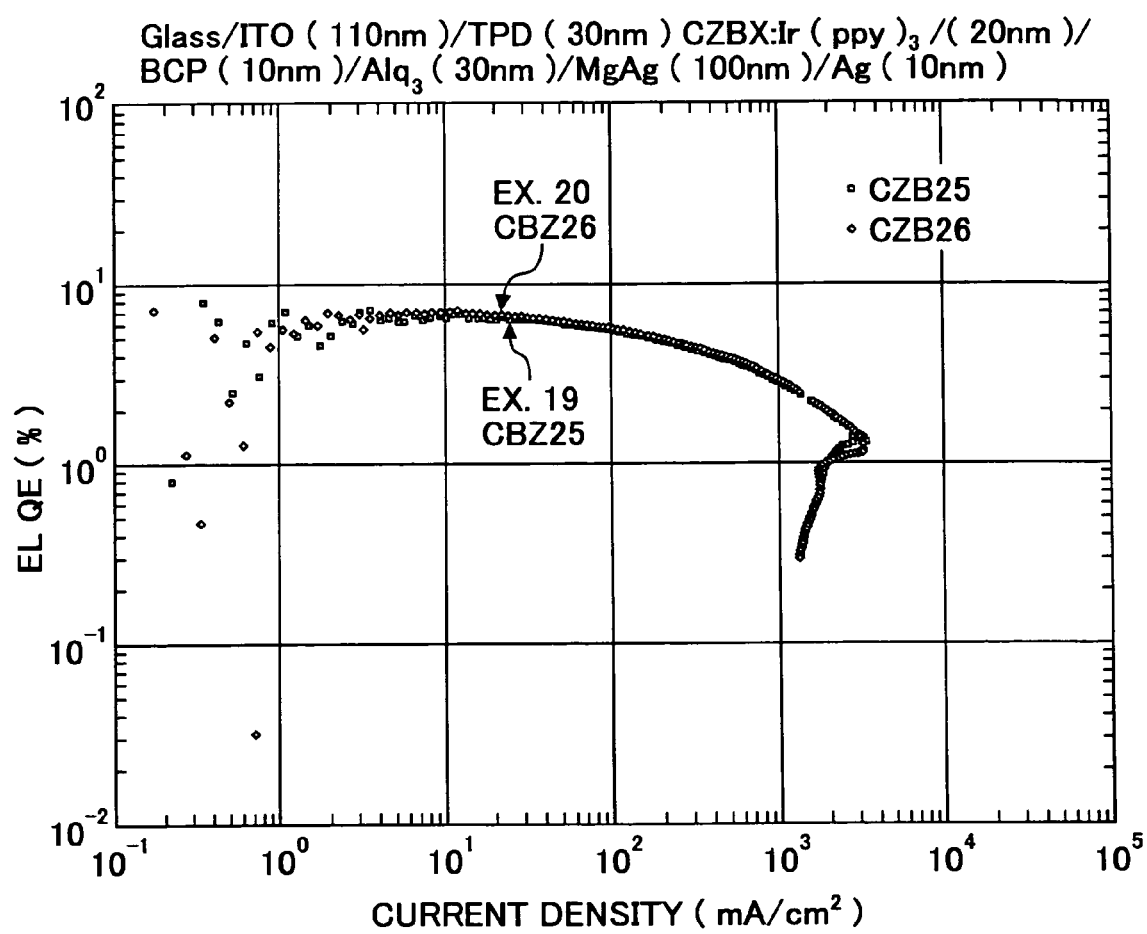
FIG. 55 is a graph showing the relationships between the current and the quantum efficiency of the organic electroluminescent devices of Examples 19 and 20.

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of $10^{-4}$ Pa to form a hole transporting layer with a thickness of 50 nm on the substrate. Subsequently, CBZ25 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 55 and the maximum quantum efficiency is 6.9%.

Figure 56:
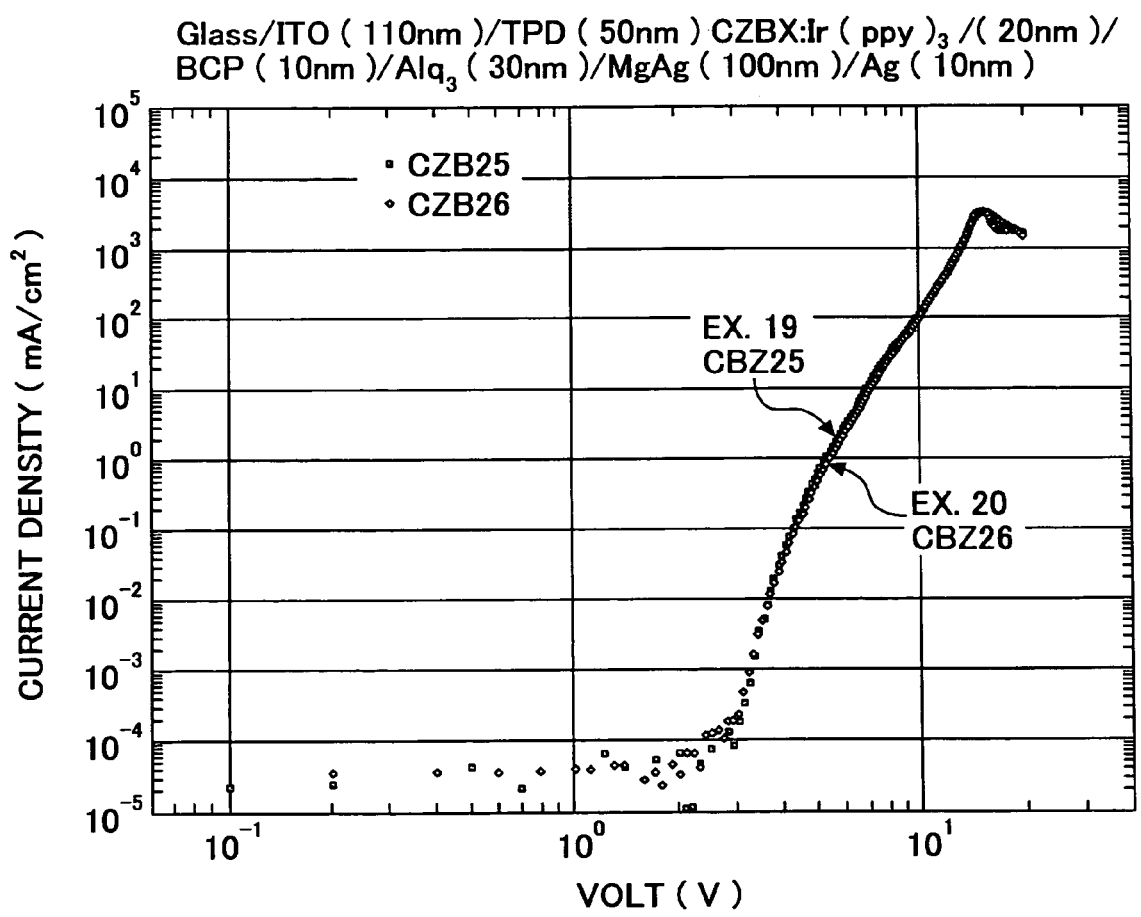
FIG. 56 is a graph showing the relationships between the current and the voltage of the organic electroluminescent devices of Examples 19 and 20.
Figure 57:
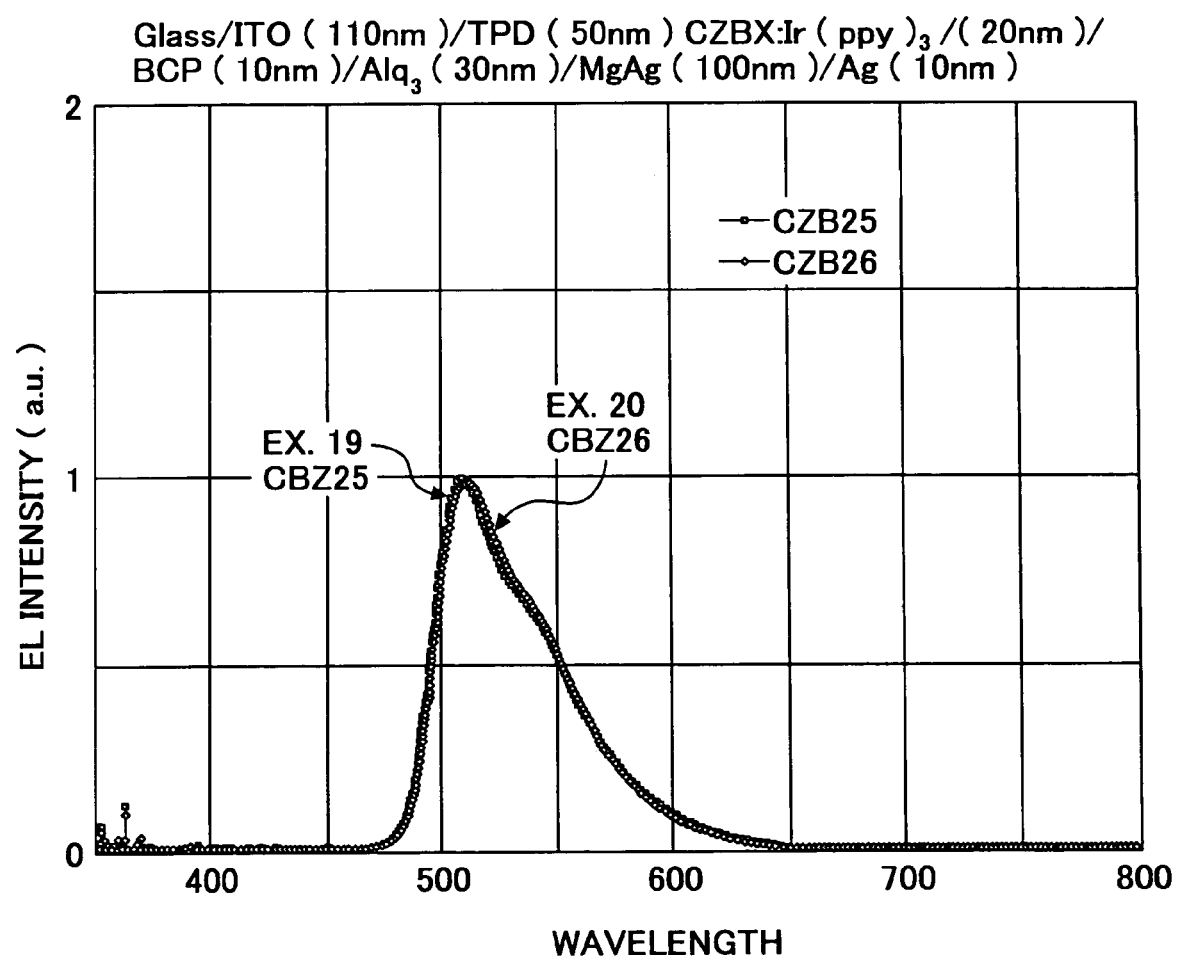
FIG. 57 is a graph showing the emission spectra of the organic electroluminescent devices of Examples 19 and 20.

In addition, the device has an excellent current-voltage characteristic as shown in FIG. 56. In addition, light having an emission spectrum such that a peak is observed at 515 nm was emitted from Ir(ppy)$_3$ as shown in FIG. 57.

EXAMPLE 20

An ITO substrate having a film thickness of 110 nm was adequately washed with a neutral detergent, acetone, and isopropanol, followed by washing in boiled isopropanol. The substrate was treated for 12 minutes in a UV-ozone chamber, and was put into a vapor deposition apparatus. TPD was deposited in a vacuum of $10^{-4}$ Pa to form a hole transporting layer with a thickness of 50 nm on the substrate. Subsequently, CBZ26 and Ir(ppy)$_3$ were co-deposited to form a luminescent layer with a thickness of 20 nm on the hole transporting layer. At this time, the concentration of Ir(ppy)$_3$ was kept at 6 percent by weight. Furthermore, an electron transporting layer was formed thereon by depositing BCP with a thickness of 10 nm and Alq3 with a thickness of 30 nm. Finally, a cathode was formed by depositing MgAg/Ag having a film thickness of 100/10 nm through a shadow mask. Thus, an electroluminescent device was prepared. The current-quantum efficiency property of the device is shown in FIG. 55 and the maximum quantum efficiency is 7.3%.

In addition, the device has an excellent current-voltage characteristic as shown in FIG. 56. In addition, light having an emission spectrum such that a peak is observed at 515 nm was emitted from Ir(ppy)$_3$ as shown in FIG. 57.

This document claims priority and contains subject matter related to Japanese Patent Applications Nos. 2003-373745, 2003-314495, 2003-373735, 2004-245423 and 2004-245438, filed on Oct. 31, 2003, Sep. 5, 2003, Oct. 31, 2003, Aug. 25, 2004 and Aug. 25, 2004, respectively, incorporated herein by reference.

Having now fully described the invention, it will be apparent to one of ordinary skill in the art that many changes and modifications can be made thereto without departing from the spirit and scope of the invention as set forth therein.

What is claimed as new and desired to be secured by Letters Patent of the United States is:

1. An organic electroluminescent device comprising:
   an anode;
   a cathode which faces the anode; and
   at least one layer including a luminescent layer that comprises a phosphorescent dopant and is located between the anode and the cathode,
   wherein the at least one layer includes a 3,6-diphenylcarbazole compound represented by the following formula (II) that can serve as a host material for a guest material:

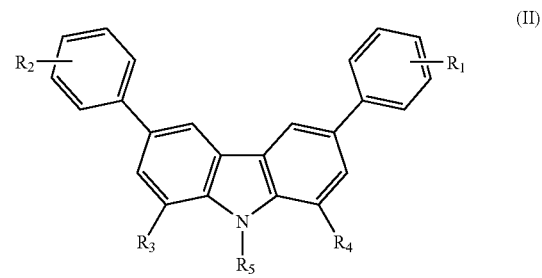

wherein R$_1$ and R$_2$ are 4-phenyl groups, R$_5$ represents a phenyl group or a biphenyl group substituted only with one or more groups selected from the group consisting of a hydrogen atom, an alkyl group, an alkoxy group and a combination thereof, and R$_3$ and R$_4$ independently represent a hydrogen atom or an unsubstituted aryl group, wherein the at least one layer includes a hole transporting layer, the luminescent layer, and an electron transporting layer, which are overlaid in this order.

2. The organic electroluminescent device according to claim 1, wherein the phosphorescent dopant is an iridium complex.

3. The organic electroluminescent device according to claim 2, wherein the iridium complex is tris(2-phenylpyridine)iridium.

4. The organic electroluminescent device according to claim 1, wherein R$_5$ is a phenyl group substituted only with one or more groups selected from the group consisting of a hydrogen atom, an alkyl group, an alkoxy group and a combination thereof.

5. The organic electroluminescent device according to claim 1, wherein R$_5$ is a biphenyl group substituted only with one or more groups selected from the group consisting of a hydrogen atom, an alkyl group, an alkoxy group and a combination thereof.

6. The organic electroluminescent device according to claim 1, wherein R$_5$ is a phenyl group.

7. The organic electroluminescent device according to claim 1, wherein R$_5$ is a biphenyl group.

8. The organic electroluminescent device according to claim 1, wherein $R_5$ is a 4-methoxyphenyl or a 3-methoxyphenyl group.

9. The organic electroluminescent device according to claim 1, wherein $R_3$ and $R_4$ are hydrogen atoms; and $R_5$ is at least one selected from the group consisting of a methylphenyl group, a biphenyl group, a methoxyphenyl group, and a phenyl group.

10. The organic electroluminescent device according to claim 1, wherein $R_1$ and $R_2$ are 4-phenyl groups and $R_5$ is a phenyl group.

* * * * *